United States Patent
Schenk et al.

(10) Patent No.: US 9,995,705 B2
(45) Date of Patent: Jun. 12, 2018

(54) AMPEROMETRIC GAS SENSOR

(71) Applicant: STERIS Corporation, Mentor, OH (US)

(72) Inventors: Elizabeth H. Schenk, Nashua, NH (US); Peter A. Burke, Concord, OH (US); Michael A. Centanni, Parma, OH (US)

(73) Assignee: Steris Corporation, Mentor, OH (US)

( * ) Notice: Subject to any disclaimer, the term of this patent is extended or adjusted under 35 U.S.C. 154(b) by 598 days.

(21) Appl. No.: 14/501,074

(22) Filed: Sep. 30, 2014

(65) Prior Publication Data

US 2015/0021203 A1   Jan. 22, 2015

Related U.S. Application Data

(62) Division of application No. 13/776,953, filed on Feb. 26, 2013, now Pat. No. 9,459,233.
(Continued)

(51) Int. Cl.
*G01N 27/407* (2006.01)
*G01N 27/30* (2006.01)
(Continued)

(52) U.S. Cl.
CPC .......... *G01N 27/4072* (2013.01); *A61L 2/208* (2013.01); *A61L 2/28* (2013.01); *G01N 27/126* (2013.01); *G01N 27/30* (2013.01); *G01N 27/301* (2013.01); *G01N 27/3335* (2013.01); *G01N 27/4074* (2013.01); *G01N 27/4076* (2013.01); *G01N 33/0036* (2013.01); *A61L 2/202* (2013.01); *A61L 2/206* (2013.01); *A61L 2202/14* (2013.01)

(58) Field of Classification Search
None
See application file for complete search history.

(56) References Cited

U.S. PATENT DOCUMENTS

| | | | |
|---|---|---|---|
| 4,123,700 | A | 10/1978 | LaConti et al. |
| 4,171,253 | A | 10/1979 | Nolan et al. |

(Continued)

FOREIGN PATENT DOCUMENTS

| | | |
|---|---|---|
| CN | 1846129 A | 10/2006 |
| EP | 0821228 | 1/1998 |

(Continued)

OTHER PUBLICATIONS

Mack et al., Thermo Fisher Scientific Application Note 51933, 2010.*

(Continued)

*Primary Examiner* — Luan V Van
*Assistant Examiner* — Steven E Rosenwald
(74) *Attorney, Agent, or Firm* — Renner, Otto, Boisselle & Sklar, LLP

(57) ABSTRACT

The disclosed invention relates to an amperometric gas sensor for measuring the concentration of an analyte, comprising: a solid support; and a working electrode in contact with the solid support; wherein the analyte comprises a dopant which when in contact with the solid support increases the electrical conductivity of the solid support. A sterilization process employing the amperometric gas sensor is disclosed.

20 Claims, 15 Drawing Sheets

Related U.S. Application Data

(60) Provisional application No. 61/663,754, filed on Jun. 25, 2012.

(51) Int. Cl.
  A61L 2/20      (2006.01)
  G01N 27/12     (2006.01)
  A61L 2/28      (2006.01)
  G01N 27/333    (2006.01)
  G01N 33/00     (2006.01)

(56) References Cited

U.S. PATENT DOCUMENTS

| | | |
|---|---|---|
| 4,444,892 A | 4/1984 | Malmros |
| 4,522,690 A | 6/1985 | Venkatasetty |
| 4,664,757 A | 5/1987 | Zupancic et al. |
| 4,822,566 A | 4/1989 | Newman |
| 4,865,717 A | 9/1989 | Setter et al. |
| 4,908,188 A | 3/1990 | Jefferis, III et al. |
| 4,910,149 A | 3/1990 | Okube et al. |
| 4,925,544 A | 5/1990 | Goldring |
| 4,948,496 A * | 8/1990 | Chand ............... G01N 27/4045 204/408 |
| 5,145,645 A | 9/1992 | Zakin et al. |
| 5,202,261 A | 4/1993 | Musho et al. |
| 5,250,439 A | 10/1993 | Musho et al. |
| 5,286,448 A | 2/1994 | Childers |
| 5,302,274 A | 4/1994 | Tomantschger et al. |
| 5,310,507 A | 5/1994 | Zakin et al. |
| 5,312,762 A | 5/1994 | Guiseppi-Elie |
| 5,322,611 A | 6/1994 | Zaromb |
| 5,338,412 A | 8/1994 | Burk et al. |
| 5,352,574 A | 10/1994 | Guiseppi-Elie |
| 5,372,785 A | 12/1994 | Johnson et al. |
| 5,389,336 A | 2/1995 | Childers |
| 5,445,792 A | 8/1995 | Rickloff et al. |
| 5,527,446 A | 6/1996 | Kosek et al. |
| 5,527,508 A | 6/1996 | Childers et al. |
| 5,608,156 A | 2/1997 | Ando et al. |
| 5,651,922 A | 7/1997 | Nahass et al. |
| 5,683,570 A | 11/1997 | Pacey et al. |
| 5,756,879 A | 5/1998 | Yamagishi et al. |
| 5,766,787 A | 6/1998 | Watanabe et al. |
| 5,766,934 A | 6/1998 | Guiseppi-Elie |
| 5,849,174 A | 12/1998 | Sanghera et al. |
| 5,882,590 A * | 3/1999 | Stewart ............... A61L 2/28 422/105 |
| 5,958,214 A | 9/1999 | Nikolskaja |
| 6,189,368 B1 | 2/2001 | Ichida et al. |
| 6,241,873 B1 | 6/2001 | Namba et al. |
| 6,303,096 B1 | 10/2001 | Yamamoto et al. |
| 6,517,775 B1 | 2/2003 | Wang et al. |
| 6,537,491 B1 | 3/2003 | Wang et al. |
| 6,558,529 B1 | 5/2003 | McVey et al. |
| 6,581,435 B2 | 6/2003 | Wang et al. |
| 6,631,333 B1 | 10/2003 | Lewis et al. |
| 6,844,742 B2 | 1/2005 | Centanni |
| 6,933,733 B2 | 8/2005 | Korenev et al. |
| 6,946,852 B2 | 9/2005 | Centanni |
| 7,828,956 B2 | 11/2010 | Ding et al. |
| 7,918,977 B2 | 4/2011 | Dorisio Deininger et al. |
| 2002/0014410 A1 | 2/2002 | Silveri et al. |
| 2003/0049165 A1 | 3/2003 | Yamamoto et al. |
| 2003/0086820 A1 * | 5/2003 | McDonnell .......... A61K 31/327 422/28 |
| 2004/0026246 A1 | 2/2004 | Chapples et al. |
| 2004/0129562 A1 | 7/2004 | Shuk et al. |
| 2004/0262170 A1 | 12/2004 | Centanni |
| 2005/0063882 A1 | 3/2005 | Centanni et al. |
| 2005/0170255 A1 | 8/2005 | Koh et al. |
| 2005/0244696 A1 | 11/2005 | Kuromatsu et al. |
| 2006/0096871 A1 | 5/2006 | Manoukian et al. |
| 2006/0254908 A1 * | 11/2006 | Grant ............... G01N 27/4076 204/400 |
| 2007/0102294 A1 | 5/2007 | Dorisio Deininger et al. |
| 2007/0144236 A1 | 6/2007 | Stokes et al. |
| 2008/0047847 A1 | 2/2008 | Schmidt et al. |
| 2008/0218047 A1 | 9/2008 | Buczynski et al. |
| 2009/0084159 A1 | 4/2009 | Sun et al. |
| 2009/0101501 A1 | 4/2009 | Tao et al. |
| 2009/0212782 A1 | 8/2009 | Silveri |
| 2009/0317724 A1 | 12/2009 | Kumar et al. |
| 2010/0304215 A1 | 12/2010 | Suh et al. |
| 2011/0076192 A1 | 3/2011 | Robitaille et al. |
| 2016/0363557 A1 | 12/2016 | Schenk et al. |

FOREIGN PATENT DOCUMENTS

| | | |
|---|---|---|
| EP | 1542299 | 6/2005 |
| EP | 2136431 | 12/2009 |
| JP | 06160343 | 6/1994 |
| JP | 8201336 | 8/1996 |
| JP | 10123082 | 5/1998 |
| JP | 2000097906 | 4/2000 |
| JP | 2003344347 | 12/2003 |
| JP | 2008512661 | 4/2008 |
| JP | 2009500609 | 1/2009 |
| JP | 2010003694 | 1/2010 |
| JP | 4794170 | 8/2011 |
| JP | 2011235153 | 11/2011 |
| WO | WO 2008-118564 A1 | 10/2008 |
| WO | 2009005252 | 1/2009 |

OTHER PUBLICATIONS

Official Action for corresponding Chinese Application No. 201380033413.3 dated Jan. 6, 2016 and its partial English translation.

Official Action for corresponding Japanese Application No. 2015-520175 dated Mar. 1, 2016 and its partial English translation.

Official Action for corresponding Canadian Application No. 2,876,577 dated Jan. 14, 2016.

Patent Examination Report for corresponding Australian Patent Application No. 2013281144, dated Jun. 30, 2015.

Sadek et al., Sensors and Actuators, 2007.

Official Action for corresponding Japanese Application No. 2015-520175 dated Aug. 2, 2016 and its partial English translation.

MacDiarmid et al.; "The Concept of 'Doping' of Conducting Polymers: The Role of Reduction Potentials"; Philosophical Transactions of the Royal Society of London, Series A, Mathematical and Physical Sciences, vol. 314, Issue 1528, pp. 3-14, 1985. (Abstract).

International Preliminary Report on Patentability, corresponding application PCT/US2013/36066, dated Sep. 23, 2014.

STERIS; Low Temperature Sterilization; STERIS® VHP® MD Series Sterilization System brochure; Publication date unknown. Applicants admit this is prior art.

STERIS; VHP® MD Series Low Temperature Sterilizers for Medical Devices brochure; Nov. 1, 2003.

Stetter; "Amperometric Gas Sensors—A Review"; Chem. Rev. 2008; pp. 352-366.

ZEUS Technical Whitepaper; Dielectric Properties of Polymers; Zeus Industrial Products, Inc.; 2005.

MacDiarmid et al.; "The Concept of 'Doping' of Conducting Polymers: The Role of Reduction Potentials"; Philosophical Transactions of the Royal Society of London, Series A, Mathematical and Physical Sciences, vol. 314, Issue 1528, pp. 3-14.

City Technology CiTiceL Sensor; Hampshire, UK; Jun. 11, 2011; http://222.citytech.com/PDF-Datasheets/cnlh.pdf.

Toniolo et al.; "Amperometric monitoring of hydrogen peroxide in workplace atmospheres by electrodes supported on ion-exchange membranes"; Journal of Electroanalytical Chemistry 514 (2001), pp. 123-128.

Kuwata et al.; "Detection of gaseous hydrogen peroxide using planar-type amperometric cell at room temperature"; Sensors and Actuators B 65 (2000); pp. 325-326.

Chang; "Amperometric Gas Sensors"; Talanta, vol. 40, No. 4, pp. 461-477; 1993.

(56) References Cited

OTHER PUBLICATIONS

Litt; National Science Foundation presentation; "New Polymer Electrolytes"; Nov. 14, 2001.

Gofer et al.; "Electrochemistry in Ultrahigh Vacuum: Intercalation of Lithium into the Basal Plane of Highly Oriented Pyrolytic Graphite from a Poly(ethylene oxide)/$LiClO_4$ Solid Polymer Electrolyte"; The Journal of Physical Chemistry; vol. 99, No. 31, Aug. 3, 1995; pp. 11797-11800.

Gofer et al.; Underpotential Deposition of Lithium of Polycrystalline Gold from a $LiClO_4$/Poly(ethylene oxide) Solid Polymer Electrolyte in Ultrahigh Vacuum; J. Phys. Chem., 1995, 99; pp. 11739-11741.

Invitation to Pay Additional Fees with Partial International Search Report; Application No. PCT/US2013/036066; dated Jul. 4, 2013.

Wiedemair et al.; "Toward a hydrogen peroxide sensor for exhaled breath analysis"; Procedia Engineering; vol. 25, (2011)Jan. 8, 2012; pp. 116-119.

Lange et al.; "Conducting polymers in chemical sensors and arrays"; Analytica Chimica Acta, Elsevier, Amsterdam, NL; vol. 614, No. 1, Apr. 28, 2008; pp. 1-26.

Second Written Opinion of the International Preliminary Examining Authority, Application PCT/US2013/36066, dated May 27, 2014.

Miller et al.; "Nanostructured Tin Dioxide Materials for Gas Sensor Applications"; In: "Functional Nanomaterials"; Dec. 31, 2006; America Scientific Publishers; pp. 1-24.

International Search Report and Written Opinion, application PCT/US2013/36066, dated Aug. 28, 2013.

Wiedemair et al.; "Toward a hydrogen peroxide sensor for exhaled breath analysis"; SciVerse ScienceDirect;Procedia Engineering 25 (2011); pp. 116-119.

Lange et al.; "Conducting polymers in chemical sensors and arrays"; Analytica Chimica Acta 614 (2008); pp. 1-26.

Pratt; "Applications of Conducting Polymers"; http://homepage.dtn.ntl.com/colin.pratt/applcp.htm; Aug. 18, 2003.

Pratt; "Conducting Polymers"; http://homepage.dtn.ntl.com/colin.pratt/cpoly.htm; Feb. 22, 1996.

Current claims of related U.S. Appl. No. 15/246,827, filed Aug. 25, 2016.

Office Action dated Jan. 11, 2018 for related U.S. Appl. No. 15/246,827.

Official Action for corresponding European Application No. 13717150.0 dated Feb. 7, 2018.

Lu X et al., "Solid-state amperometric hydrogen sensor based on polymer electrolyte membrane fuel cell", Sensors and Actuators B, vol. 107, Jun. 20, 2005, pp. 812-817.

* cited by examiner

AMPEROMETRIC GAS SENSOR

This application is a divisional of and claims priority under 35 U.S.C. § 120 to copending, commonly assigned U.S. application Ser. No. 13/776,953, filed Feb. 26, 2013, which claims priority to U.S. provisional patent application 61/663,765, filed Jun. 25, 2012. These applications are incorporated herein by reference.

TECHNICAL FIELD

This invention relates to amperometric gas sensors.

BACKGROUND

Sterilizations employing vaporized hydrogen peroxide (hereinafter sometimes referred to as VHP) in a vacuum chamber have been used in validated pharmaceutical aseptic productions and research applications.

SUMMARY

The currently available methods for sensing VHP concentration as a sterilization parameter in a vacuum are limited. Electrochemical methods exist, such as a DragerSensor $H_2O_2$ LC sensor, manufactured by Därgerwerk AG. & Co. KGaA, Burkard Dillig, 23558 Lübeck, Germany, but this method employs liquid-based electrolytes which precludes their use in a sterilization conducted in a vacuum. Generally, where solid polymer electrolytes are employed in electrochemical methods, the ionic conductivity of the polymer is dependent upon the hydration of the polymer, as with Nafion (an ionomer in the form of a sulfonated tetrafluorothylene based fluoropolymer-copolymer), or upon the addition of salt moieties, as in high-ionic conductivity polymer electrolytes employed with solid-state batteries. Neither of these is suitable for use in a sterilization process conducted in a vacuum. The water employed with Nafion would evaporate. Failure to attain the apparently mutually exclusive properties of high-ionic conductivity and good mechanical strength via the formation of salt containing polymers precludes use of such salt containing polymers in sterilizations conducted in a vacuum. Good mechanical strength is needed for electrolytes that will be required to withstand the vacuum cycling (e.g., lowest pressure may be about 4 Torr) and elevated temperatures (e.g., about 60° C.) that would typically be used in a sterilization process conducted in a vacuum. These problems are overcome with the present invention.

This invention relates to an amperometric gas sensor for measuring the concentration of an analyte, comprising: a solid support; and a working electrode in contact with the solid support; wherein the analyte comprises a dopant which when in contact with the solid support increases the electrical conductivity of the solid support. In an embodiment, the sensor further comprises a reference electrode. In an embodiment, the solid support comprises a polymer. In an embodiment, at least a portion of the solid support is amorphous. In an embodiment, at least a portion of the solid support is crystalline. The solid support may comprise an insulator or a semi-conductor prior to being contacted by the analyte. While not wishing to be bound by theory, it is believed that the analyte functions as both the analyte and as a dopant. Thus, by exposing the solid support to the analyte, the solid support is converted to an electrolyte with sufficient ionic conductivity to allow the amperometric gas sensor to function as an electrochemical cell. This was unexpected.

In an embodiment, the sensor is relatively small enough so that uncompensated resistance may be negligible and a two electrode sensor can be employed. This allows for a simplified sensor design and minimization of stray current pickup.

In any of the above-indicated embodiments, prior to being contacted by the analyte, the solid support is characterized by the absence of a dopant. The term "absence of dopant" refers to a solid support that contains no dopant, or contains one or more dopants at a concentration level that would be considered to be only a trace amount or at an impurity level, for example, no more than about 0.1% by weight, or no more than about 0.01% by weight, or no more than about 0.001% by weight.

In any of the above-indicated embodiments, the solid support is characterized by the absence of salt. The term "absence of salt" refers to a solid support that contains no salt, or contains one or more salts at a concentration level that would be considered to be only a trace amount or at an impurity level, for example, no more than about 0.1% by weight, or no more than about 0.01% by weight, or no more than about 0.001% by weight.

In any of the above-indicated embodiments, the solid support comprises a porous solid, the volume of voids in the porous solid divided by the total volume of the porous solid being in the range up to about 0.7, or from about 0.1 to about 0.7, or from about 0.3 to about 0.65.

In any of the above-indicated embodiments, the solid support comprises a polymer that is a non-conductive polymer prior to being contacted by the analyte.

In any of the above-indicated embodiments, the solid support comprises poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly (acrylnitrile-butadiene-styrene), polyvinyl chloride, chlorinated polyether, poly(chlorotrifluoro ethylene), glass, ceramic, carbon, graphite, or a mixture of two or more thereof.

In any of the above-indicated embodiments, the working electrode comprises a noble metal, for example, gold, platinum, iridium, palladium, osmium, silver, rhodium, ruthenium, titanium, or a mixture of two or more thereof.

In any of the above-indicated embodiments, the reference electrode comprises a noble metal, for example, gold, platinum, iridium, palladium, osmium, silver, rhodium, ruthenium, titanium, or a mixture of two or more thereof.

In any of the above-indicated embodiments, the analyte comprises an oxidizing gas or a reducing gas. The analyte may comprise vaporous hydrogen peroxide, ethylene oxide, ozone, or a mixture of two or more thereof. The analyte may comprise a hydrogen-containing gas. The analyte may comprise atomic hydrogen, hydrogen sulfide, hydrogen sulfite, ammonia, carbon monoxide, oxalic acid, formic acid, ascorbic acid, phosphorous acid, or a mixture of two or more thereof.

In any of the above-indicated embodiments, the solid support comprises poly(ethylene terphthalate), the working electrode comprises palladium, and the analyte comprises vaporous hydrogen peroxide.

In any of the above-indicated embodiments, the solid support is in the form of a poly (ethylene terephthalate) film with a thickness in the range from about 0.05 to about 0.6 mm, or from about 0.07 to about 0.5 mm, or from about 0.1 to about 0.3 mm, or about 0.25 mm.

In any of the above-indicated embodiments, the sensor further comprises a reference electrode, and the working electrode and the reference electrode are formed by sputtering palladium on the solid support, the solid support comprising a poly(ethylene terephathalate) film.

In any of the above-indicated embodiments, the sensor further comprises a reference electrode, and the working electrode and the reference electrode comprise palladium, the thickness of the reference electrode and the working electrode being in the range from about 40 to about 150 nanometers, or from about 80 to about 120 nanometers, or about 100 nanometers.

In any of the above-indicated embodiments, the sensor further comprises a reference electrode and the solid support comprises a poly (ethylene terephathalate) film, the working electrode and the reference electrode comprising palladium electrodes sputtered on the poly (ethylene terephthalate) film; the thickness of the electrodes being in the range from about 40 to about 150 nanometers, or from about 80 to about 120 nanometers, or about 100 nanometers; the thickness of the poly (ethylene terephthalate) film being in the range from about 0.05 to about 0.6 mm, or from about 0.07 to about 0.5 mm, or from about 0.1 to about 0.3 mm, or about 0.25 mm; and the separation between the electrodes being from about 0.7 to about 0.9 mm, or about 0.88 mm.

In any of the above-indicated embodiments, the sensor comprises a working electrode and a reference electrode, the working electrode being connected to a potential control to maintain a stable voltage potential at the working electrode with respect to the reference electrode. The reference electrode may be connected to a current amplifier. The current amplifier may be connected to a current follower to convert gas concentration-related current to a voltage.

The invention relates to a method for determining the concentration of a gaseous analyte in an enclosed space, the method comprising: placing the amperometric gas sensor of any of the above-indicated embodiments in the enclosed space; flowing the analyte in contact with the sensor; and determining the concentration of the analyte in the enclosed space using the amperometric gas sensor. The analyte may comprise an oxidizing gas or a reducing gas. The analyte may comprise vaporous hydrogen peroxide, ethylene oxide, ozone, or a mixture of two or more thereof. The analyte may comprise a hydrogen-containing gas. The analyte may comprise atomic hydrogen, hydrogen sulfide, hydrogen sulfite, ammonia, carbon monoxide, oxalic acid, formic acid, ascorbic acid, phosphorous acid, or a mixture of two or more thereof. The pressure within the enclosed space may be below atmospheric pressure (e.g., about 0.1 to about 750 Torr), atmospheric pressure, or above atmospheric pressure (e.g., absolute pressure of about 1 to about 2 atmospheres).

The invention relates to a method for determining the concentration of a sterilant gas in a vacuum chamber during a sterilization process, the method comprising: placing the amperometric gas sensor of any of the above-indicated embodiments in the vacuum chamber; conducting the sterilization process in the vacuum chamber under a vacuum using the sterilant gas; and determining the concentration of the sterilant gas in the vacuum chamber using the amperometric gas sensor. In an embodiment, the sterilant gas flows in the vacuum chamber and contacts the amperometric gas sensor. In an embodiment, the sterilant gas is mixed with a carrier gas to form a gaseous mixture, and the gaseous mixture flows in the vacuum chamber and contacts the amperometric sensor. In an embodiment, pulses of the sterilant gas flow into the vacuum chamber and contact the amperometric gas sensor. In an embodiment, pulses of a gaseous mixture comprising the sterilant gas and a carrier gas flow into the vacuum chamber and contact the amperometric gas sensor. In any of the above-indicated embodiments, the sterilant gas may comprise vaporous hydrogen peroxide, ethylene oxide, ozone, or a mixture of two or more thereof. The sterilant gas may further comprise an alkaline gas. The sterilant gas may comprise a mixture of vaporous hydrogen peroxide and ammonia.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION OF PREFERRED EMBODIMENT

Figure 1:
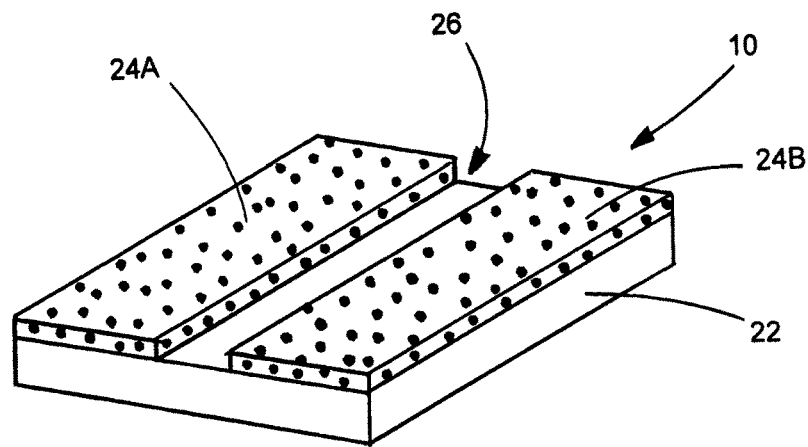
FIG. 1 is a perspective view of an amperometric gas sensor according to an embodiment of the invention.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "sterilization" refers to rendering a substance incapable of reproduction, metabolism and/or growth. The term "sterilization" includes microbial deactivation. While sterilization is often taken to refer to a total absence of living organisms, the term may be used herein to refer to a substance free from living organisms to a degree agreed to be acceptable. The term "sterilization" may be used herein to also refer to processes less rigorous than sterilization, for example, disinfection, sanitization, decontamination, cleaning, and the like. Variations of the term "sterilization," such as sterilant, sterilizing, etc., may also be used herein to refer to and encompass related variants associated with sterilization processes as well as processes less rigorous than sterilization (e.g., disinfectant, disinfecting, etc.).

The term "non-conductive polymer" is used herein to refer to a polymer or copolymer characterized by a volume resitivity of at least about $10^5$ ohm-cm, or at least about $10^6$ ohm-cm, or at least about $10^7$ ohm-cm, or at least about $10^8$ ohm-cm, or at least about $10^9$ ohm-cm, or at least about $10^{10}$ ohm-cm, or at least about $10^{11}$ ohm-cm, or at least about $10^{12}$ ohm-cm, or at least about $10^{13}$ ohm-cm, as determined by ASTM D257-07. Specific non-conductive polymers and copolymers that may be used, and their corresponding volume resistivity values include:

| Polymer | Volume Resistivity (ohm-cm) |
|---|---|
| Polyethylene Low density | $10^{15}$-$10^{18}$ |
| Polyethylene Medium density | $10^{15}$-$10^{18}$ |
| Polyethylene High density | $6 \times 10^{15}$-$10^{18}$ |
| Polypropylene | $6.5 \times 10^{16}$ |
| Acrylic resins | $>10^{14}$ |
| High impact Acrylic resins | $10^{16}$-$10^{17}$ |
| Polystyrene | $10^{17}$-$10^{21}$ |
| Polystyrene high Impact resin | $10^{13}$-$10^{17}$ |
| Poly(styrene-acrylonitrile) | $10^{15}$ |
| Poly(acrylonitrile-butadiene-styrene) | $10^{12}$-$10^{17}$ |
| Polyvinyl chloride | $>10^9$ |
| Chlorinated polyether | $1.5 \times 10^{16}$ |
| Poly(chlorotrifluoroethylene) | $10^{18}$ |
| Fluorinated poly(ethylene-propylene) | $>10^{18}$ |
| Poly(ethylene terephthalate) | $>10^{14}$ |
| Polycarbonate | $1.7 \times 10^5$ |

The term "solid support" refers to a solid material that is used to support an electrode. The solid support may comprise a solid electrolyte when contacted by an analyte that comprises a dopant. The solid support may be an insulator or a semi-conductor and be transformed to a solid electrolyte upon being contacted with an analyte that comprises a dopant.

The term "solid electrolyte" refers to a solid material which conducts electricity when placed between electrodes and a voltage is applied.

The term "dopant" refers to a material which when in contact with a solid support increases the electrical conductivity of that solid support. A dopant may contact a solid support and oxidize (p-doping) or reduce (n-doping) the solid support.

The term "amorphous solid" is used herein to refer to a solid material that lacks the long-range order characteristic of a crystal. Amorphous solids may include ceramics, glass, polymers, nanostructured materials, and the like.

The term "insulator" is used herein to refer to a material whose internal electric charges do not flow freely and therefore do not conduct an electric current under the influence of an electric field. There are no perfect insulators, but glass, paper and some polymers which have high resistivity characteristics are considered to be insulators for purposes of this invention. The non-conductive polymers referred to above are insulators for purposes of this invention.

The term "semiconductor" is used herein to refer to a material which has an electrical conductivity between that of a conductor such as copper and an insulator such as glass.

Current conduction in a semiconductor may occur via free electrons and "holes," collectively known as charge carriers. The doping of a semiconducting material may increase the number of charge carriers within it. When a doped semiconductor contains excess holes it may be called "p-type," and when it contains excess free electrons it may be called "n-type." A single semiconductor crystal can have multiple p- and n-type regions.

The term "electricity" is used herein to refer to the motion of ions and/or electrons in an electric field.

The term "electrical conductivity" refers to ionic conductivity and/or electronic conductivity.

The term "vacuum" is used herein to refer to a pressure that is below atmospheric pressure. The pressure, in terms of absolute pressure, in the vacuum may be in the range from about 0.1 to about 750 Torr, or from about 0.1 to about 700 Torr, or from about 0.1 to about 600 Torr, or from about 0.1 to about 500 Torr, or from about 0.1 to about 400 Torr, or from about 0.1 to about 300 Torr, or from about 0.1 to about 200 Torr, or from about 0.1 to about 100 Torr, or from about 1 to about 75 Torr, or from about 1 to about 50 Torr, or from about 1 to about 25 Torr, or from about 3 to about 25 Torr, or from about 5 to about 25 Torr, or from about 5 Torr to about 20 Torr.

Referring to the drawings, FIG. 1 is a perspective view of an amperometric gas sensor in accordance with the present invention. Amperometric gas sensor 10 includes solid support 22, and electrodes 24A and 24B positioned on the solid support 22. The electrode 24A is a working electrode. The electrode 24B is a reference electrode. A space or gap 26 separates the electrodes 24A and 24B.

Figure 2:
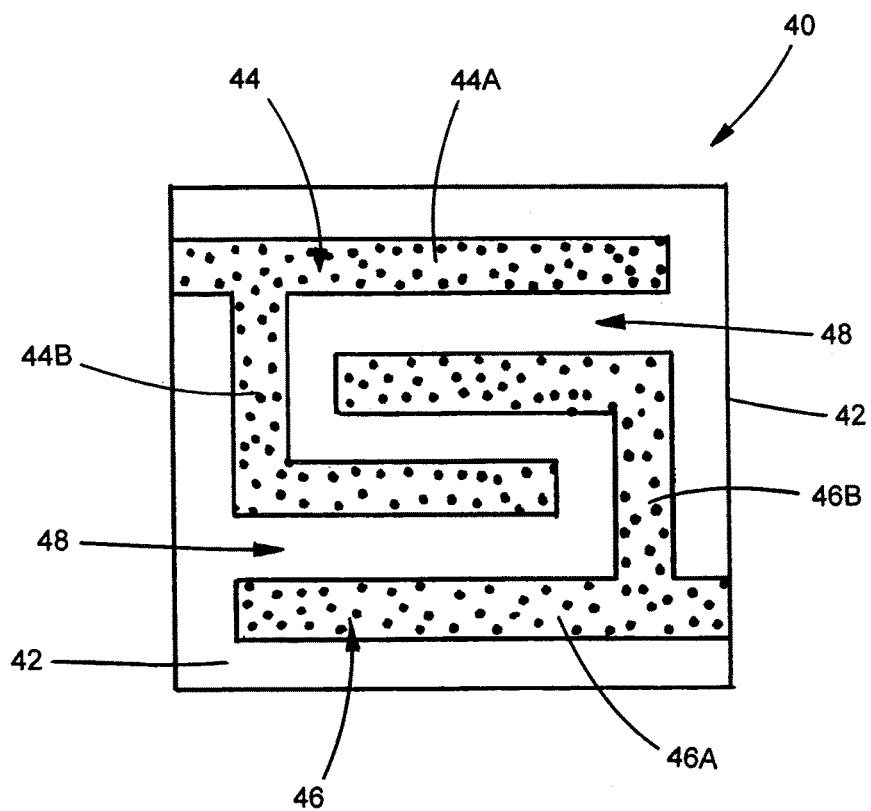
FIG. 2 is a top plan view of an amperometric gas sensor according another embodiment of the invention.

An alternate embodiment of the inventive amperometric gas sensor is illustrated in FIG. 2. Referring to FIG. 2, amperometric gas sensor 40 includes solid support 42 and electrodes 44 and 46 positioned on the solid support 42. Electrode 44 is a working electrode which includes elongated straight strip portion 44A and an L-shaped arm portion 44B that extends from strip portion 44A. Electrode 46 is a reference electrode which includes elongated straight strip portion 46A and an L-shaped arm portion 46B that extends from strip portion 46A. Electrodes 44 and 46 are positioned on solid support 42 such that arm portion 44B of electrode 44 is between strip portion 46A and arm portion 46B of electrode 46, and arm portion 46B of electrode 46 is between strip portion 44A and arm portion 44B of electrode 44. A space or gap 48 separates electrodes 44 and 46. The electrodes 44 and 46 may be interdigitally spaced in order to achieve higher signal strength in a small sensor area.

Figure 3:
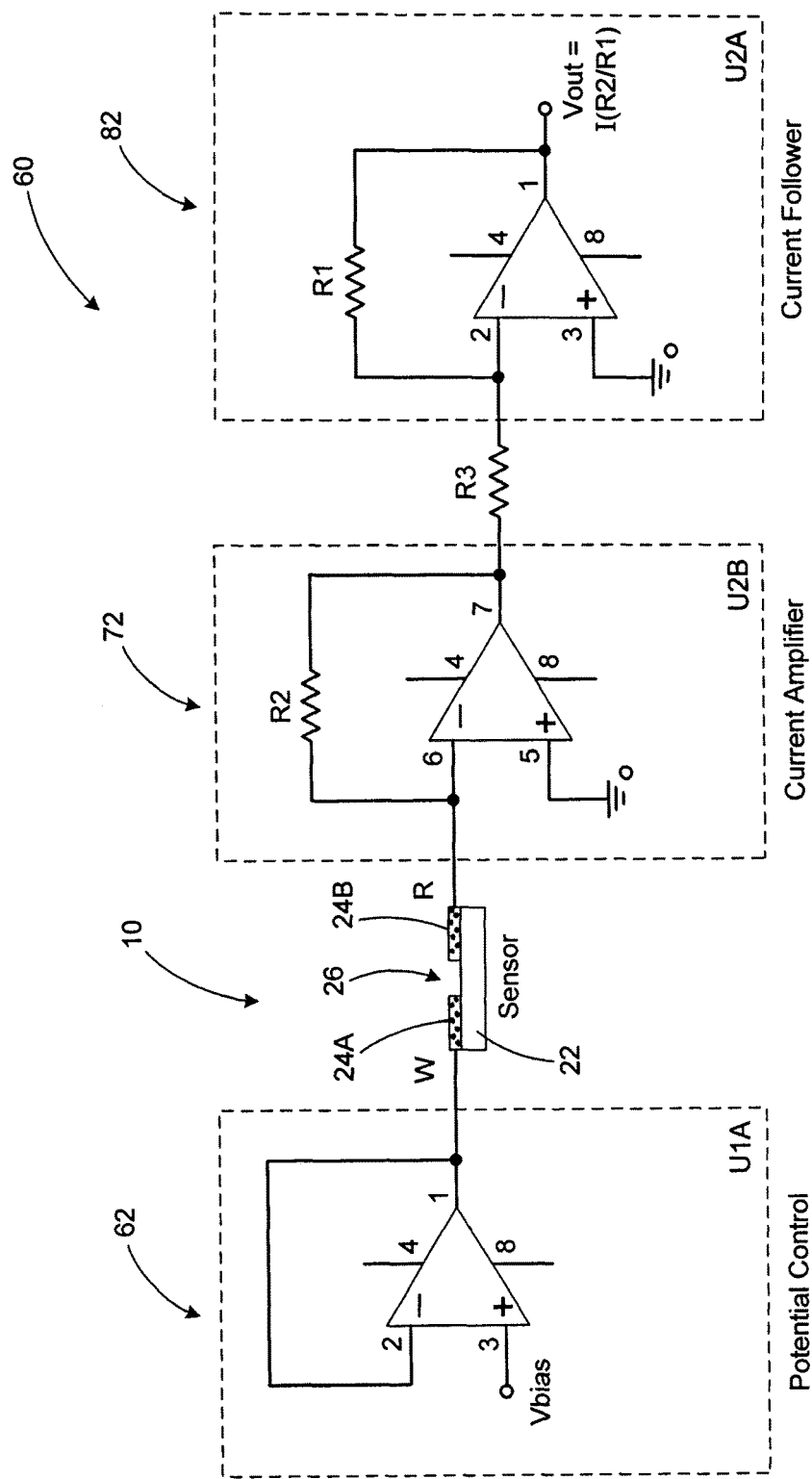
FIG. 3 is a block diagram of a control circuit for use with an amperometric gas sensor according to the invention.

Referring to FIG. 3, a block diagram of a control circuit 60 for controlling amperometric gas sensor 10 is shown. Sensor 10 is illustrated in FIG. 3, but amperometric gas sensor 40 could be substituted for sensor 10. Control circuit 60, known as a potentiostat, is shown for a two electrode sensor configuration. Control circuit 60 includes potential control 62, current follower 72, and current amplifier 82. Potential control 62 may be provided to maintain a stable voltage potential at the working electrode with respect to the reference electrode at the formal reduction potential necessary for the desired reaction to occur. The reduction voltage may be minimal, i.e., about 0.682 V for hydrogen peroxide. Current follower 72 may be provided to convert the gas concentration-related current from sensor 10 to a voltage and to process further signal processing. Current amplifier 82 may be provided to enable measuring of low-level currents of the nA and pA ranges. DC power for sensor control circuit 60 may be a battery or an AC adapter.

In an embodiment, the electrodes shown in FIGS. 1 and 2 may be formed using laser ablation techniques. The use of laser ablation allows for the creation of extremely small feature sizes to be accurately manufactured in a repeated manner. The sensors disclosed in FIGS. 1 and 2 may be formed by scribing sputtered films (e.g., palladium sputtered poly(ethylene terphthalate) films) using laser ablation.

In an embodiment, the electrodes of the inventive amperometric sensor may be supported and surrounded by the solid support, except for the ends or edges of the electrodes which may remain free for exposure to the analyte and for connection to the potentiostat circuit. The electrodes may be wires that are relatively small in diameter and length. They may be placed parallel to each other and as close as possible so that uncompensated resistance along the current path is insignificant. The solid support and the electrodes may lie in a plane, as shown in FIGS. 1 and 2.

The solid support may comprise an insulator or a semiconductor prior to being contacted by the analyte. In an embodiment, at least a portion of the solid support may be amorphous. For example, from about 5 to about 30% by volume of the solid support may be amorphous, or from about 10 to about 25% by volume may be amorphous. In an embodiment, at least a portion of the solid support may be crystalline. The solid support may contain one or more amorphous layers in contact with one or more crystalline layers. Prior to being contacted by the analyte, the solid support may be characterized by the absence of a dopant. The solid support may be characterized by the absence of any salt moiety. The solid support may be porous, with the volume of voids in the porous solid divided by the total volume of the porous solid being in the range up to about 0.7, or from about 0.1 to about 0.7, or from about 0.3 to about 0.65.

The solid support may comprise a polymer that is a non-conductive polymer prior to being contacted by the analyte. The solid support may comprise poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly (styrene-acrylonitrile), poly(acrylonitrile-butadiene-styrene), polyvinyl chloride, chlorinated polyether, poly(chlorotrifluoro ethylene), or a mixture of two or more thereof. The solid support may comprise glass and/or ceramic. The solid support may comprise carbon and/or graphite.

The solid support may comprise any of the above-indicated polymers and one or more fillers. The fillers may be electrically conductive or non-conductive. The fillers may be inorganic, organic, or a mixture thereof.

The inorganic fillers may comprise one or more silicates, oxides, carbonates, sulfates, hydroxides, carbons, metals, glass, mixtures of two or more, and the like. Examples of the inorganic fillers that may be used include clay, talc, mica, asbestos, feldspar, bentonite clay, wollastonite, fuller's earth, pumice, pyrophillite, rottenstone, slate flour, vermiculite, calcium silicate (precipitated), magnesium silicate (precipitated), aluminum oxide, hydrated alumina, antimony trioxide, magnesium oxide, titanium dioxide, zinc oxide, silica, quartz, diatomaceous earth, tripoli, pyrogenic, hydrogel, aeorgel, calcium carbonate (precipitated), ground limestone, ground marble, barium carbonate (precipitated), magnesium carbonate (precipitated), barium sulfate, barytes, blanc fixe, calcium sulfate, calcium hydroxide, magnesium hydroxide, carbon black, furnace black, lampblack, acetylene, graphite, carbon fibers, metal powders (e.g., copper, aluminum, bronze, lead, zinc, steel), metal fibers, metal whiskers, metal wire, barium ferrite, magnetite, molybdenum disulfide, glass fibers, glass flakes, ground glass, mixtures of two or more thereof, and the like.

The organic fillers that may be used may include ground bark, processed lignin, keratin, soybean meal, nylon fibers, acrylic fibers, fluorocarbon polymer fibers, polyester fibers, wood flour, shell flours, alpha cellulose fibers, cotton flock fibers, sisal fibers, jute fibers, rayon fibers, mixtures of two or more thereof, and the like.

When the fillers are electrically conductive, the amount of filler in the solid support may be up to about 20% by volume, or in the range from about 0.01 to about 20 percent by volume, or from about 0.02 to about 18 percent by volume.

In an embodiment, the solid support may comprise one or more of the above-indicated polymers and one or more of the above-indicated electrically conductive fillers, and the volume concentration of the one or more electrically conductive fillers in the solid support is less than the percolation threshold for electrical conductivity of the solid support. Thus, for example, if the solid support were to comprise poly(ethylene terephthalate) (PET) and one or more electrically conductive fillers, the conductivity of the solid support would be dependent on the conductivity of the PET when the volume concentration of the electrically conductive fillers in the solid support is below the percolation threshold for the solid support. On the other hand, if the volume concentration of the electrically conductive fillers in the solid support exceeded the percolation threshold for the solid support, the conductivity of the solid support would be dependent on the conductivity of the electrically conductive fillers.

In an embodiment, the solid support may comprise a crystalline polymer represented by the formula $$(PEO)_6\text{-}LiSbF_6$$

wherein PEO refers to poly(ethylene oxide). This polymer may be electrically conductive. While not wishing to be bound by theory, it is believed that the polymer chains fold to form cylindrical tunnels inside of which the lithium ions are coordinated by the ether oxygens, while the anions are located outside of the tunnels with no coordinating interactions with the cations. Enhanced ionic conductivity of the crystalline material may thus result from the relatively free movement of cations through the tunnels.

The diffusion of the anayte through the solid support to the electrode interface may be a rate-limiting step. For a fast response time, the thickness of the solid support may be maintained as thin as possible to provide for fast diffusion (cm$^2$/s) and yet maintain the desired mechanical strength properties needed to handle the sensor in both manufacturing and in use. The thickness of the solid support may be in the range from about 0.05 to about 0.6 mm, or from about 0.07 to about 0.5 mm, or from about 0.1 mm to about 0.3 mm, or about 0.25 mm.

The inventive amperometric gas sensor may be considered to be an electrochemical cell in which faraday currents are flowing, causing (or caused by) chemical reactions at the electrodes, which are separated by the solid support. The working electrode is where the half reaction of interest with the analyte may take place. The reference electrode is essentially nonpolarizable. The electrode reactions are controlled by the voltage between the metal of the electrodes and the solid support. Control of the potential of the working electrode with respect to the reference electrode may be equivalent to observing or controlling the energy of the electrons within the working electrode. A more negative potential at the working electrode (with respect to the reference electrode) raises the energy level; a more positive potential (with respect to the reference electrode) lowers the energy level. If the electrons reach a high enough energy level, they will transfer from the working electrode to vacant electronic states in the solid support, creating a flow of electrons from the electrode to the solid support (a reduction current). Similarly, if the energy of the electrons is lowered enough, electrons in the solid support will transfer to the working electrode (an oxidation current). Oxidation cannot take place without reduction, and vice-versa. A feature of the inventive amperometric gas sensor is that the simultaneously occurring oxidation-reduction reactions are spatially separated. The electrode reaction may occur in several series and parallel reaction steps. There may be three steps in a series: (1) the gaseous analyte is transported to the electrode surface from the bulk of the solid support (usually predominantly by diffusion, but it may also occur by electromigration), (2) a charge transfer reaction occurs, and (3) the product is transported from the electrode surface to the bulk of the solid support. A potentiostat circuit may be used for potential control across the electrodes as well as for measuring the resulting current through the sensor. The magnitude of the current generated by the electrochemical reaction at the working electrode is proportional to the analyte concentration in the gas being sampled.

A problem with many amperometric gas sensors that are currently available is that they do not support operation in the vacuum state, as a water reservoir of some sort is typically needed to maintain ionic conductivity in, for example, the Nafion or gel-type electrolytes that are currently in use. For amperometric gas concentration measurements in a vacuum environment, a solid electrolyte is necessary for leak free use, convenient packaging, and sustainability, as any water would evaporate quickly. For example, in the vacuum conditions seen in medical sterilization systems with VHP at 50° C., the vapor pressure of water is about 11 Torr. The conductivity of Nafion is dependent on humidity, being up to about 1000 times stronger at 100% relative humidity than at 20% relative humidity (at room temperature); thus in the vacuum state, performance would vary. Gel electrolytes, too, will vary in conductivity with humidity at a given temperature, often by more than an order of magnitude from saturation to dry air. The inventive amperometric sensor provides a solution to this problem by being suitable for use in processes conducted in a vacuum. Going beyond that, the inventive amperometric sensor may also be used in processes conducted at atmospheric pressure, and in processes involving pressures above atmospheric pressure.

The inventive amperometric gas sensor may be used to determine the concentration of one or more analytes in the form of oxidizing gases, reducing gases, and the like, that are present in an enclosed space. The analyte may comprise vaporous hydrogen peroxide, ethylene oxide, ozone, or a mixture of two or more thereof. The analyte may comprise a hydrogen-containing gas. The analyte may comprise atomic hydrogen, hydrogen sulfide, hydrogen sulfite, ammonia, carbon monoxide, oxalic acid, formic acid, ascorbic acid, phosphorous acid, or a mixture of two or more thereof. The pressure within the enclosed space may be atmospheric or above atmospheric, for example, an absolute pressure in the range from about 1 to about 2 atmsopheres. The pressure within the enclosed space may be below atmospheric pressure. The pressure, in terms of absolute pressure, may be in the range from about 0.1 to about 750 Torr, or from about 0.1 to about 700 Torr, or from about 0.1 to about 600 Torr, or from about 0.1 to about 500 Torr, or from about 0.1 to about 400 Torr, or from about 0.1 to about 300 Torr, or from about 0.1 to about 200 Torr, or from about 0.1 to about 100 Torr, or from about 1 to about 75 Torr, or from about 1 to about 50 Torr, or from about 1 to about 25 Torr, or from about 3 to about 25 Torr, or from about 5 to about 25 Torr, or from about 5 Torr to about 20 Torr. The temperature within the enclosed space may be in the range from about 15 to about 90° C., or from about 30 to about 70° C., or from about 45° C. to about 65° C., or from about 50° C. to about 60° C.

The inventive amperometric gas sensor may be particularly suited for use in sterilization processes employing a sterilant gas wherein the sterilization is conducted in a vacuum. These sterilization processes may be particularly suited for sterilizing articles of complex and irregular shapes, for example, articles with narrow apertures, holes, tubes, open ended lumens, internal cavities, deadlegs, flat surfaces, and the like. Numerous medical devices (e.g., endoscopes), dental instruments, and the like, are characterized by such complex and irregular shapes.

It is generally desired to sterilize medical devices, dental instruments, and the like, before use. In medical and dental facilities, where medical devices and dental instruments need to be used several times per day on different patients, it is important not only to sterilize the instruments between patients to prevent cross-contamination, but to do so quickly and economically without damaging the instruments.

Several different methods have been developed for delivering a sterilant gas to the vacuum chamber of a sterilizer for sterilizing medical devices, dental instruments, and the like. The sterilant gas may comprise any sterilant gas that is useful for these sterilizations. These may include vaporized hydrogen peroxide (VHP), ethylene oxide, ozone, or a mixture of two or more thereof. The sterilant gas may be mixed with an alkaline gas such as ammonia. The sterilant gas may comprise a mixture of vaporized hydrogen peroxide and ammonia. The sterilant gas may be mixed with a carrier gas. The carrier gas may comprise air, nitrogen, and the like.

The sterilization process may comprise any sterilization process or sterilization cycle, where the process allows sterilant vapor to be carried into, through, and out of the sterilization vacuum chamber from a vaporizer, with or without carrier gas, during a portion of the cycle. The sterilization process may involve varying vacuum chamber pressures during a sterilization cycle or from cycle-to-cycle. For example, the sterilization process may employ a combination deep vacuum/flow-through cycle, in which the chamber pressure increases as the cycle progresses from deep vacuum to flow-through conditions, through a transition phase. The rate of pressure increase, and the actual pressure levels obtained may vary during such a cycle or from such cycle-to-cycle, depending, for instance, on the nature of the instrument load (i.e., the degree of flow restriction presented by the load).

VHP may be used as the sterilant gas in the sterilization process. The VHP may be generated from an aqueous solution of hydrogen peroxide. The aqueous solution may comprise from about 30% to about 40% by weight hydrogen peroxide, and from about 60% to about 70% by weight water. By adding an alkaline gas that is soluble in the hydrogen peroxide (ammonia, for example), the pH of the sterilant may be controlled. The presence of hydrogen peroxide in the sterilant may serve to lower the pH (e.g., 35% aqueous hydrogen peroxide solution has a pH of about 3 to about 4) and the ammonia may be added to raise the pH to a value of about 8 to about 9. The volumetric ratio of VHP to ammonia gas may be in the range from about 1:1 to about 1:0.0001.

VHP, when used in combination with ammonia gas, may be referred to as modified VHP or mVHP. VHP and/or mVHP may be effective against microbial and chemical decontaminants because they may provide a broad spectrum of activity against a wide variety of pathogenic microorganisms and chemical pathogenic agents, such as hard to destroy spores of Bacillus stearothermophilus, Bacillus anthracis, smallpox virus, and the like. They may be also effective at or close to room temperature (e.g., about 15 to about 30° C.), making them suitable for use with little or no heating. VHP and/or mVHP may have good material compatibility.

The pressure within the vacuum chamber during these sterilizations may be below atmospheric pressure. The pressure, in terms of absolute pressure, may be in the range from about 0.1 to about 750 Torr, or from about 0.1 to about 700 Torr, or from about 0.1 to about 600 Torr, or from about 0.1 to about 500 Torr, or from about 0.1 to about 400 Torr, or from about 0.1 to about 300 Torr, or from about 0.1 to about 200 Torr, or from about 0.1 to about 100 Torr, or from about 1 to about 75 Torr, or from about 1 to about 50 Torr, or from about 1 to about 25 Torr, or from about 3 to about 25 Torr, or from about 5 to about 25 Torr, or from about 5 Torr to about 20 Torr.

The temperature within the vacuum chamber during these sterilizations may be in the range from about 15 to about 90° C., or from about 30 to about 70° C., or from about 45° C. to about 65° C., or from about 50° C. to about 60° C.

Sterilization processes that may be used are described in U.S. Pat. Nos. 5,286,448; 5,389,336; 5,445,792; and 5,527,508.

The level of sterilant gas concentration in the vacuum chamber of the sterilizer may determine the level of sterility attained. Thus, knowing the level of sterilant gas during a sterilization cycle may allow the state of sterility to be known faster than with post-cycle indicators, such as biological indicators.

In use for hydrogen peroxide detection, the amperometric sensor may be exposed to the sterilant gas in the vacuum chamber of the sterilizer. The gas diffuses through the solid support to the working electrode. The voltage at the working electrode with respect to the reference electrode is set by the potentiostat. For VHP, the voltage is ≥0.68 V. Hydrogen peroxide is oxidized at the working electrode. A corresponding reduction reaction occurs at the reference electrode. Current in the working electrode is measured by the potentiostat and provides a quantitative measure of the hydrogen peroxide concentration.

The inventive amperometric gas sensor may be used in sterilization processes wherein vaporized hydrogen peroxide alone is introduced and vacuum chamber pressure fluctuates between atmospheric and vacuum levels. Additionally, in various embodiments the amperometric gas sensor may be exposed to different target gases, and the electrical conditions may be selected so that reaction only occurs in the presence of the desired target gas, and not other gases that may be present in the analyte gas sample.

It may be desired to effectively and automatically control the amount of sterilant vapor delivered to a sterilization chamber, during the varying chamber pressure conditions which may be experienced during a sterilization cycle, or from cycle to cycle, to maximize sterilant vapor exposure. It may be desirable, however, that the level of sterilant vapor not exceed its saturation limit under the sterilization conditions. Otherwise, sterilant will condense, decreasing the amount of sterilant vapor available for sterilization. Also, condensed sterilant, such as hydrogen peroxide, may degrade or harm the contents of the sterilization chamber. Synthetic materials, such as are employed in flexible endoscopes, for example, may be damaged by condensed hydrogen peroxide.

The inventive amperometric gas sensor may be used to optimize the efficacy of sterilization achieved over a given period of time and/or to shorten the time required to sterilize a variety of instruments, or items which may be present or loaded into the sterilization chamber or other sealed enclosure. The sterilization process may be particularly suited for sterilizing endoscopes or other instruments having long, narrow lumens, which may provide varying degrees of flow resistance. The sterilization process may also be used to sterilize the interior of the sterilization chamber, with or without a load.

The inventive amperometric gas sensor may be used to maximize the concentration of sterilant gas in the vacuum chamber without exceeding the saturation limit for the sterilant gas in the sterilization chamber, in response to chamber pressure. By maintaining the concentration of sterilant gas at a high percentage of its saturation limit, in response to chamber pressure, cycle time can be reduced and/or greater assurance of sterilization realized.

By using the inventive amperometric gas sensor, there is no need to wait until a pre-determined pressure level is reached, before injecting sterilant at a constant rate into the system, to ensure that a pre-determined percentage of saturation limit is maintained. Instead, the sterilant can be immediately injected, at a rate adjusted to provide the predetermined saturation limit percentage, in the sterilization chamber immediately after introduction of the sterilant gas, at the chamber pressure measured prior to injection. Thus, the throughput of the sterilization process may be increased, and/or greater assurance of effective sterilization over a given period may be provided.

The rate of sterilant gas injected into the flow of a carrier gas may be automatically adjusted in response to the vacuum chamber pressure, to maintain a pre-determined maximum percentage of the saturation limit for the sterilant, during at least a portion of the sterilization cycle in which sterilant gas flows through the sterilization chamber with a carrier gas.

The contaminants that may be treated with the sterilization process may comprise one or more chemical contaminants and/or biological contaminants. Different levels of sterilization may be accomplished within the vacuum chamber. As used herein, the term "sterilization" is intended to encompass both microbial decontamination as well as chemical decontamination—the destruction of chemical agents, or their conversion to harmless or odorless compounds. For some applications, the sterilization process that is conducted may be less rigorous than a complete sterilization, for example, the sterilization may comprise disinfection, sanitization, decontamination, cleaning, and the like. Sterilization may encompass the neutralizing of unpleasant odors, such as tobacco smoke, perfume, or body odor residues, and odors and dampness due to molds. "Microbial sterilization" may be used herein to encompass the destruction of biological contaminants, specifically, living microorganisms, and also the destruction or inactivation of pathogenic forms of proteinaceous-infectious agents (prions). The term microbial sterilization encompasses sterilization, the highest level of biological contamination control, which connotes the destruction of all living microorganisms. The term sterilization also includes disinfection, the destruction of harmful microorganisms, and sanitizing, which connotes being free from germs. "Chemical sterilization" is intended to encompass the destruction of pathogenic chemical agents or their conversion to less harmful or odiferous species.

Exemplary biological contaminants which may be destroyed in the sterilization process include bacterial spores, vegetative bacteria, viruses, molds, and fungi. Some of these may be capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), mixtures of two or more thereof, and the like. Also included are *Clostridium difficile, Bacillus Stearothermophilus, Clostridium sporogenes*, mixtures of two or more thereof, and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

EXAMPLE

A series of tests are conducted to determine the relationship between (1) electric current readings obtained using amperometric sensors according to the present invention, and (2) hydrogen peroxide concentration readings obtained using a Guided Wave IR spectrophotometer. The tests are conducted in a sterilizer under vacuum conditions.

The amperometric sensors that are used are illustrated in FIG. 1. These are made using palladium sputtered PET films obtained from Conductive Technologies, Inc. of York, Pa. Referring to FIG. 1, the solid support 22 is a PET film with a thickness of 254 microns, a length of 4 mm and a width of 3 mm. The electrodes 24A and 24B are palladium electrodes which are sputtered onto the PET film. Each of the electrodes has a thickness of 100 nanometers and a width of 1.5 mm. Each electrode spans the 4 mm length of the PET film. The space 26 between the electrodes 24A and 24B is 0.88 mm.

The sterilizer is a VHP MD Series Low Temperature Sterilizer supplied by STERIS. This sterilizer is intended for use in sterilizing medical devices, dental instruments, and the like, using VHP as the sterilant under vacuum conditions. The sterilizer has a vacuum chamber wherein the articles to be sterilized are placed. The amperometric sensor is positioned in the vacuum chamber. The sterilization process, which includes injecting pulses of VHP into the vacuum chamber, is automated, and includes rapid sterilization cycle times. A microcomputer control system provides for cycle setup, selection, and monitoring.

A Keithley 6430 Sub Femptoampere SourceMeter with PreAmp is used as a potentiostat. It is connected to the amperometric sensor positioned in the vacuum chamber via coaxial cable to a vacuum feed through (AccuGlass part #111326) at a side chamber wall port of the sterilizer. Inside the vacuum chamber, the amperometric sensor is anchored in a Molex 1 mm pitch FFC/FPC Connector Part #0520430619 (using pins 3 and 4). The pins are soldered to 55 cm of stranded 22 AWG wires that end in AccuGlass push-on connectors (part #110103) which fit on the vacuum feedthrough. The vacuum feedthrough assembly is kept intact (coaxial connectors and push-on connectors) when the amperometric sensor is changed. The Guided Wave IR spectrophotometer is positioned on the chamber wall of the sterilizer.

Three or four consecutive VHP cycles are run at the injection amounts of 2.1 g, 1.7 g, 1 g of hydrogen peroxide (in the case of the three cycles), and 2.1 g, 1.7 g, 1.3 g, 1 g of hydrogen peroxide (in the case of the four cycles). Using the fourth pulse of each cycle, equations for hydrogen peroxide concentration (as read by the Guided Wave IR spectrophotometer) as a function of Δ current, as well as for the pressure Δ as a function of the Δ current, are determined for the period under vacuum. Also, the Δ in current is plotted as a function of the grams of injected hydrogen peroxide.

Current flowing through the working electrode is read every 3 seconds throughout the cycle. The Guided Wave IR spectrophotometer displays hydrogen peroxide readings every two to three seconds. The displayed reading is the average of the last ten seconds of readings. The time period for the data used in the statistical summary is from the moment VHP injection begins to the moment peak current is reached, approximately 200 seconds later. This time period begins at the last reading before the current and Guided Wave IR spectrophotometer readings spike upward. The current and Guided Wave IR Spectrophotometer readings start to respond within 10 seconds of each other. Pressure drops from atmospheric level to less than 10 Torr within 160 seconds of starting the cycle. Vacuum conditions provide a stable relative baseline in each cycle by "cleaning out" the electrolyte each time. As pressure decreases, diffusion increases.

Figure 4:
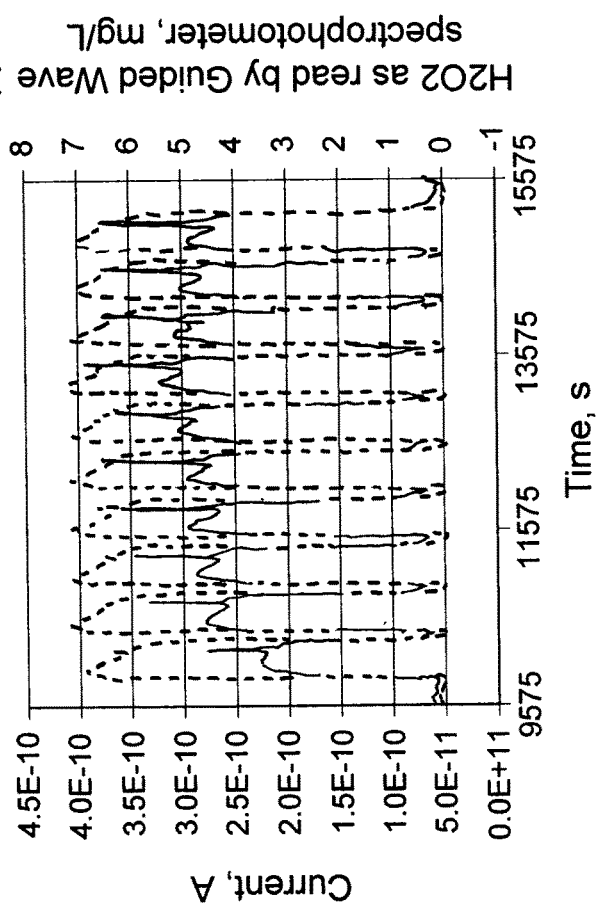
FIG. 4 is a chart showing the performance of the amperometric gas sensor disclosed in the Example with current levels determined using the amperometric gas sensor compared to hydrogen peroxide concentration levels determined using an IR spectrophotometer.

Referring to FIG. 4, the performance of the amperometric sensor is shown on the primary y-axis in the vaporized hydrogen peroxide sterilization system, with comparison on the secondary y-axis to the Guided Wave IR spectrophotometer during a sterilization cycle. The Δ of current in the constant pressure period of each pulse is also tabulated, calculated as the difference between peak current in the pulse minus the baseline current in the pulse prior to hydrogen peroxide injection. Based on the tabulated maintained average signal strength, any deterioration in the conductivity properties of the electrolyte with exposure is not evident.

Figure 5:
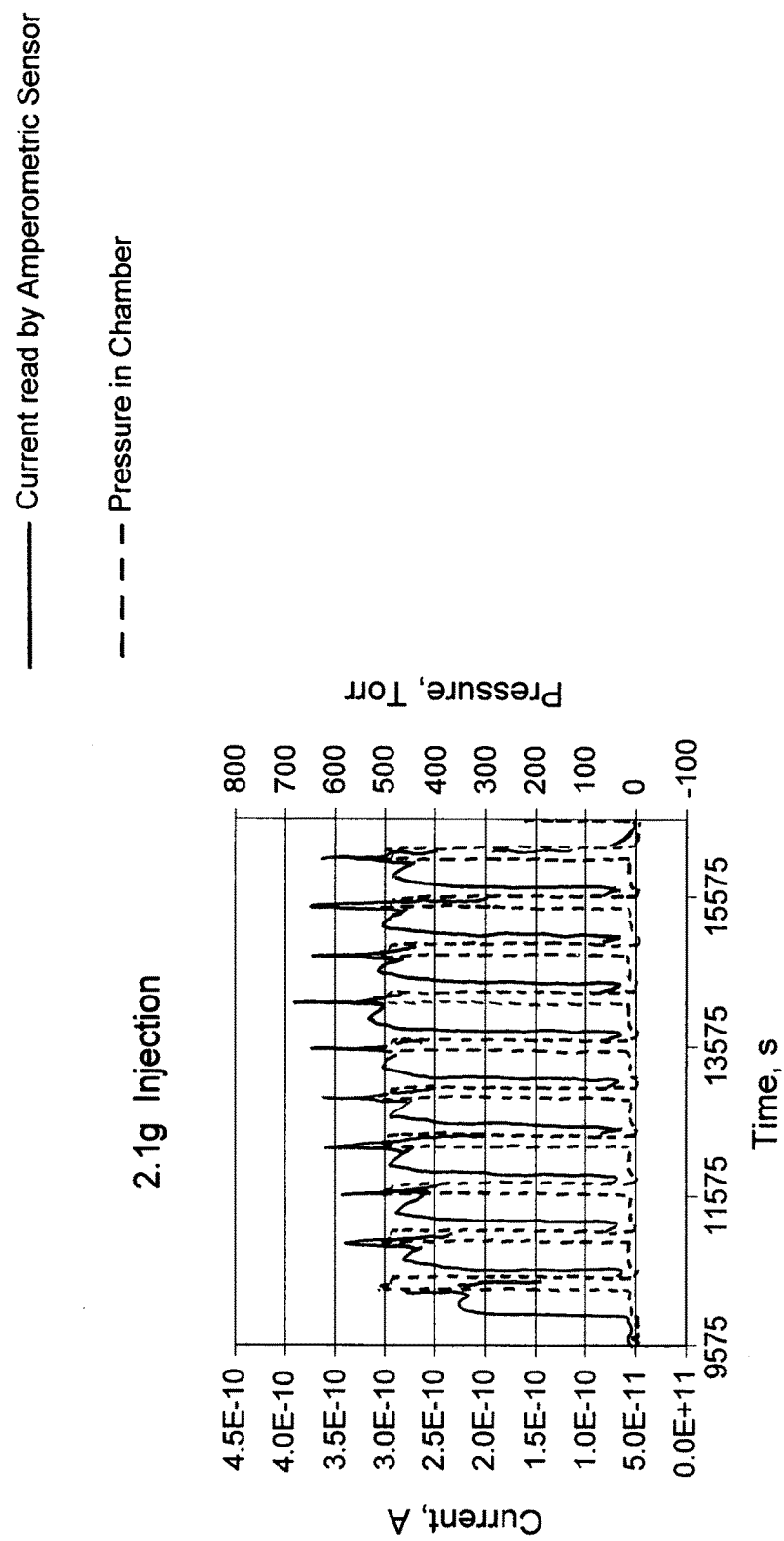
FIG. 5 is a chart showing the performance of the amperometric gas sensor disclosed in the Example wherein current levels determined by the amperometric sensor are compared to pressure levels within the vacuum chamber of the sterilizer used in the Example.
Figure 6:
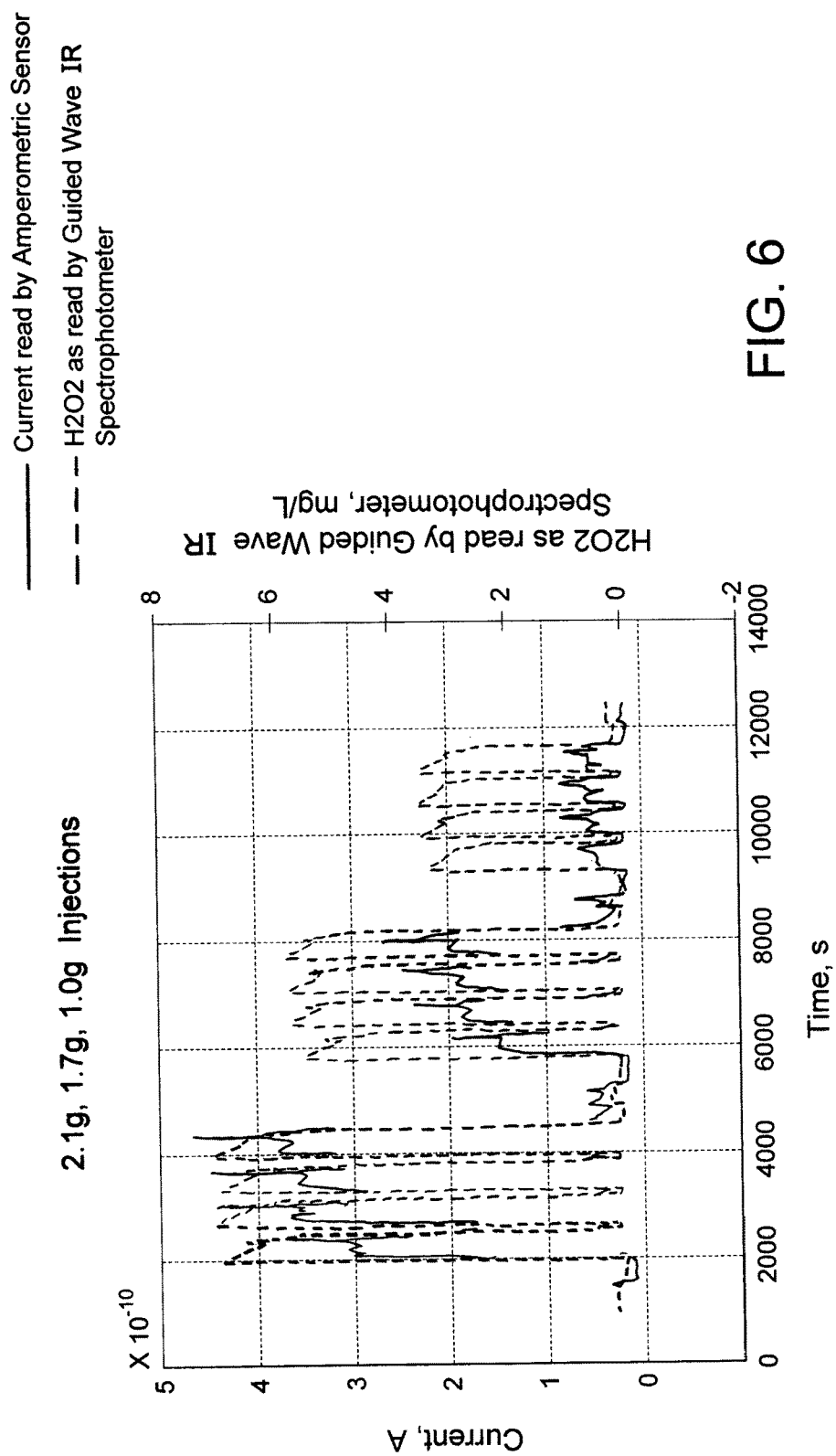
FIGS. 6-9 are charts showing the performance of the amperometric gas sensor disclosed in the Example with current levels determined with the amperometric gas sensor being compared to hydrogen peroxide concentration levels within the vacuum chamber determined using an IR spectrophotometer.
Figure 7:
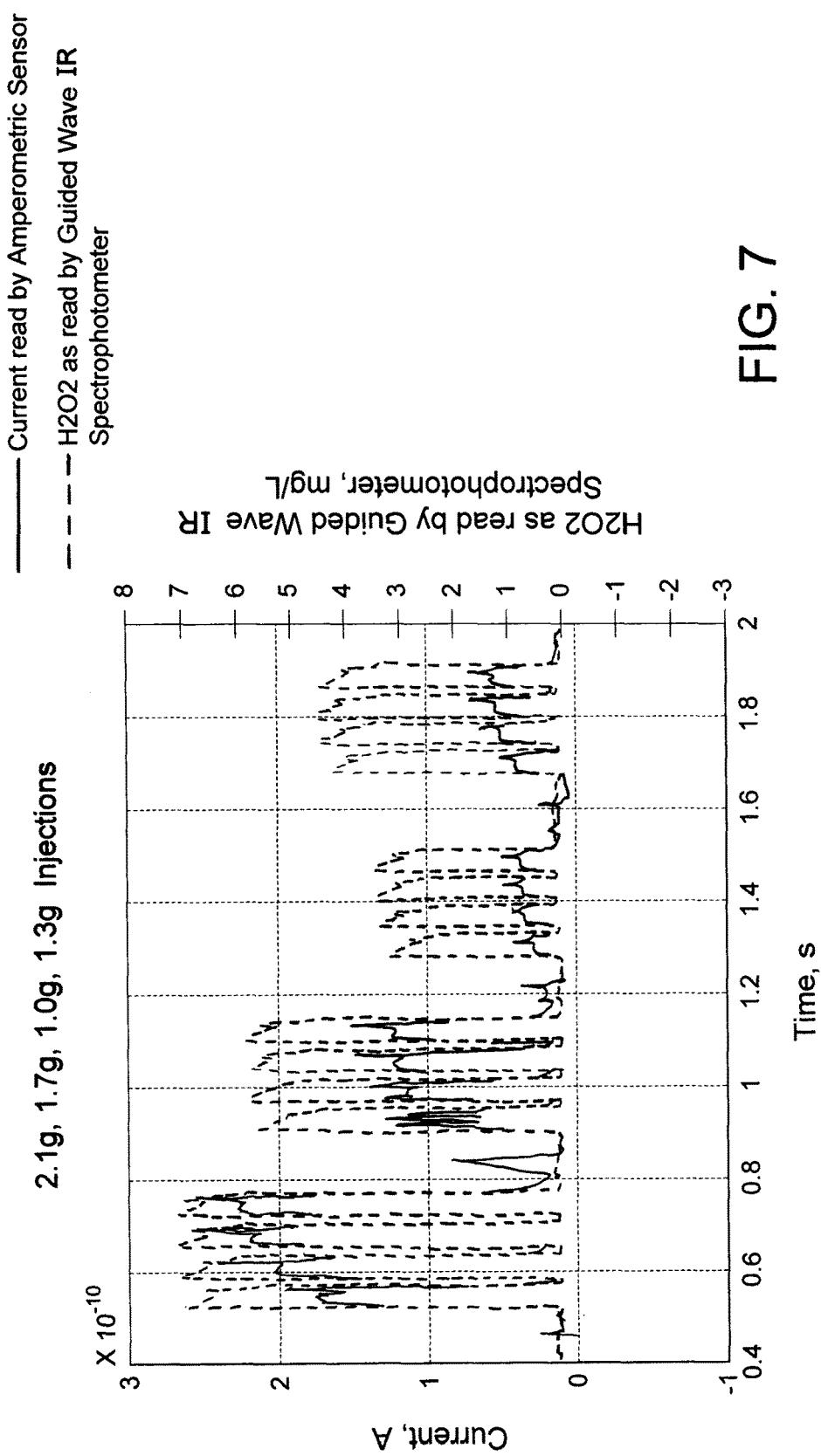
Figure 8:
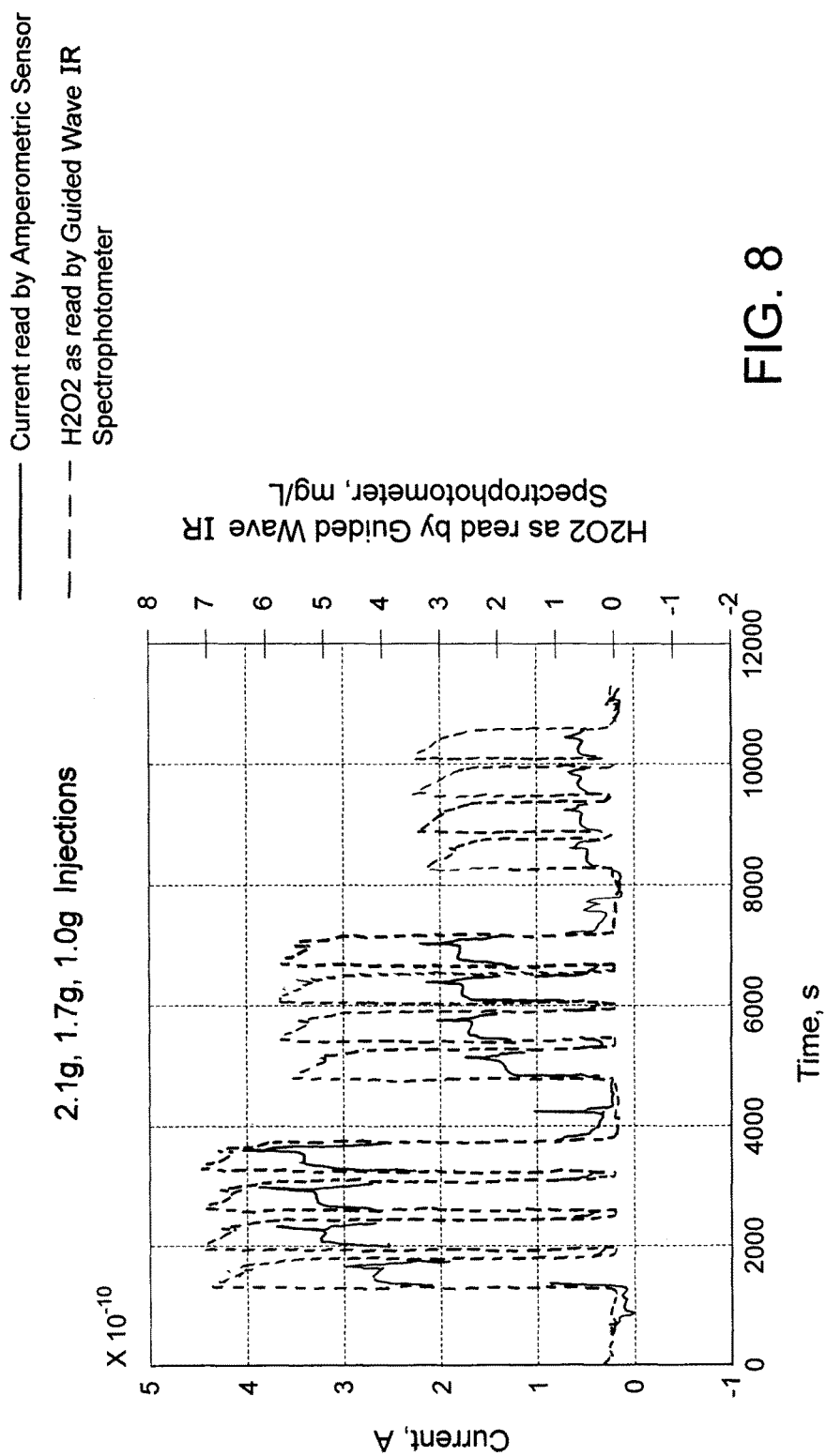
Figure 9:
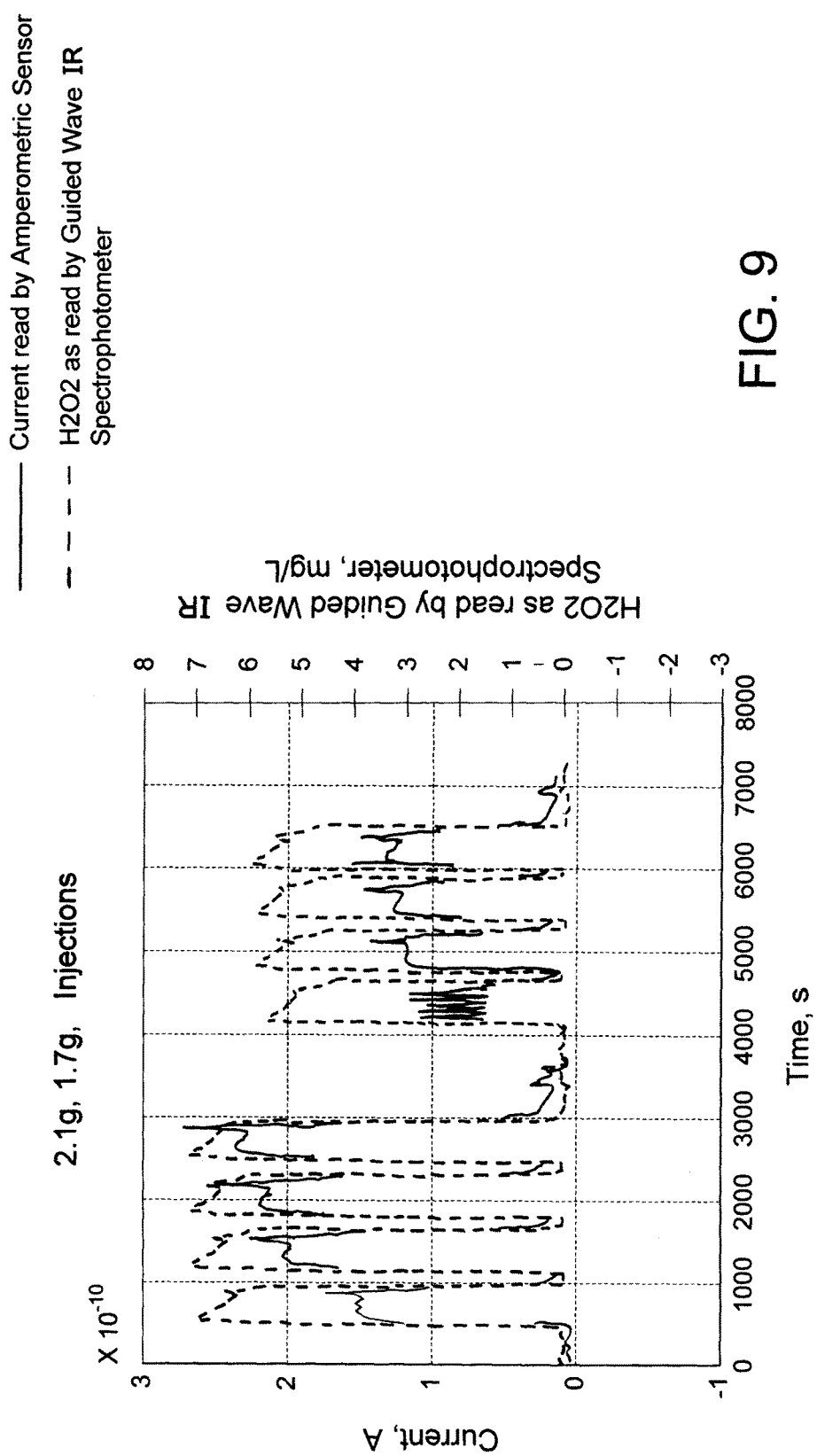

Referring to FIG. 5, the performance of the amperometric sensor is shown on the primary y-axis in the vaporized hydrogen peroxide sterilization system, with comparison on the secondary y-axis to the pressure recorded during the cycle. As the diffusion coefficient of the vaporized hydrogen peroxide passing through the PET to the solid support/electrode interface will be a constant value when the pressure is relatively constant in the vacuum chamber, and the diffusion coefficient will be a dependent variable in the current-time response, the performance of the inventive amperometric sensor is considered valid when pressure is not changing. Thus the fluctuation spike in current that occurs with the pressure change at the end of each pulse from vacuum up to atmospheric pressure as shown, is in accordance with theory.

Figure 10:
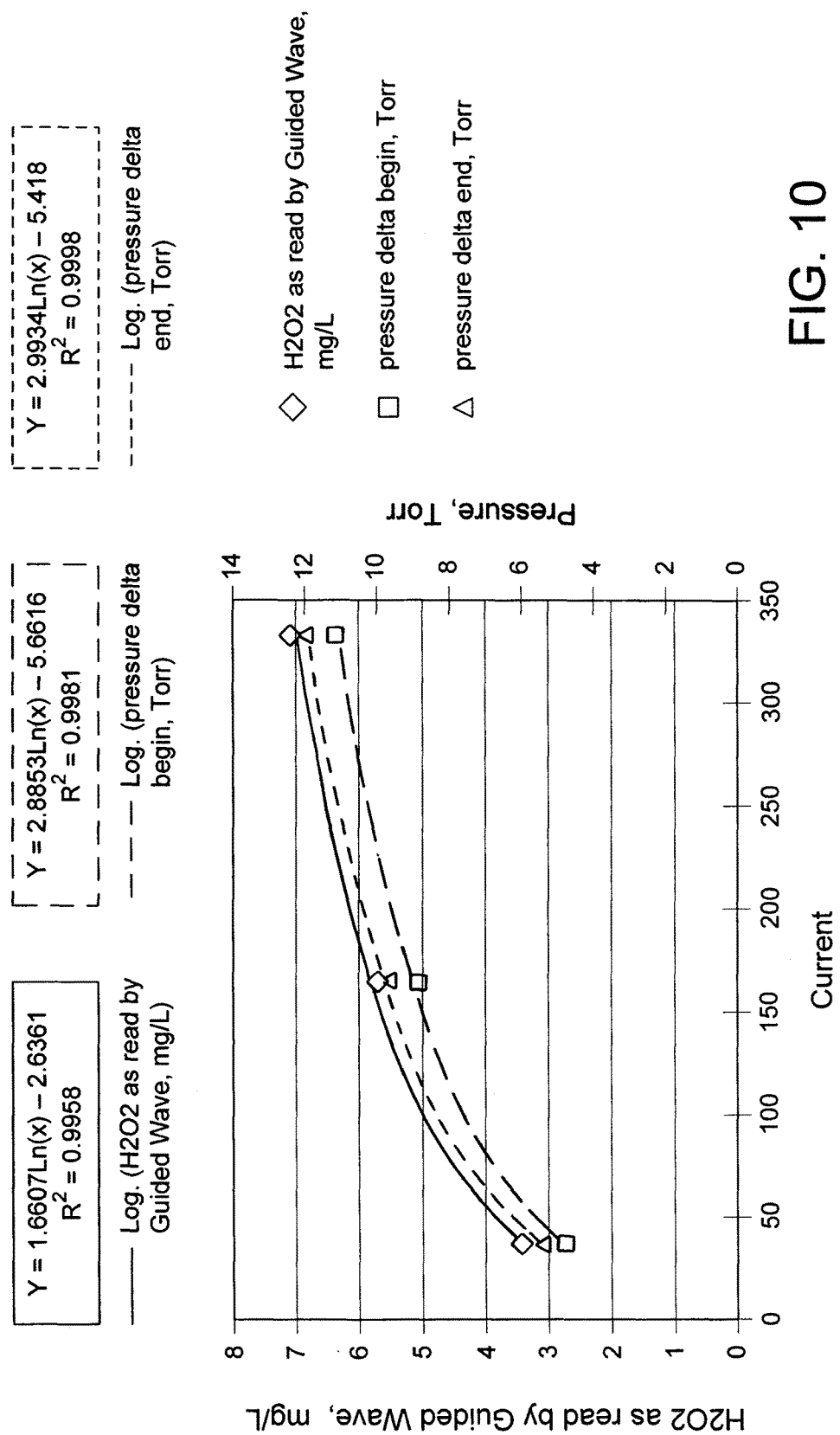
FIGS. 10-12 are charts disclosing equations provided in the Example for concentration levels of hydrogen peroxide as determined by an IR spectrophotometer and as a function of Δ current determined by the amperometric gas sensor, as well as the pressure Δ as a function of the Δ current. The disclosed values are calculated with Excel and Matlab for the period under vacuum. Excel is a software program available from Microsoft. Matlab is a software program available from MathWorks of Natich, Mass. The charts in FIGS. 10-12 use the raw data in FIGS. 6-8, respectively.
Figure 11:
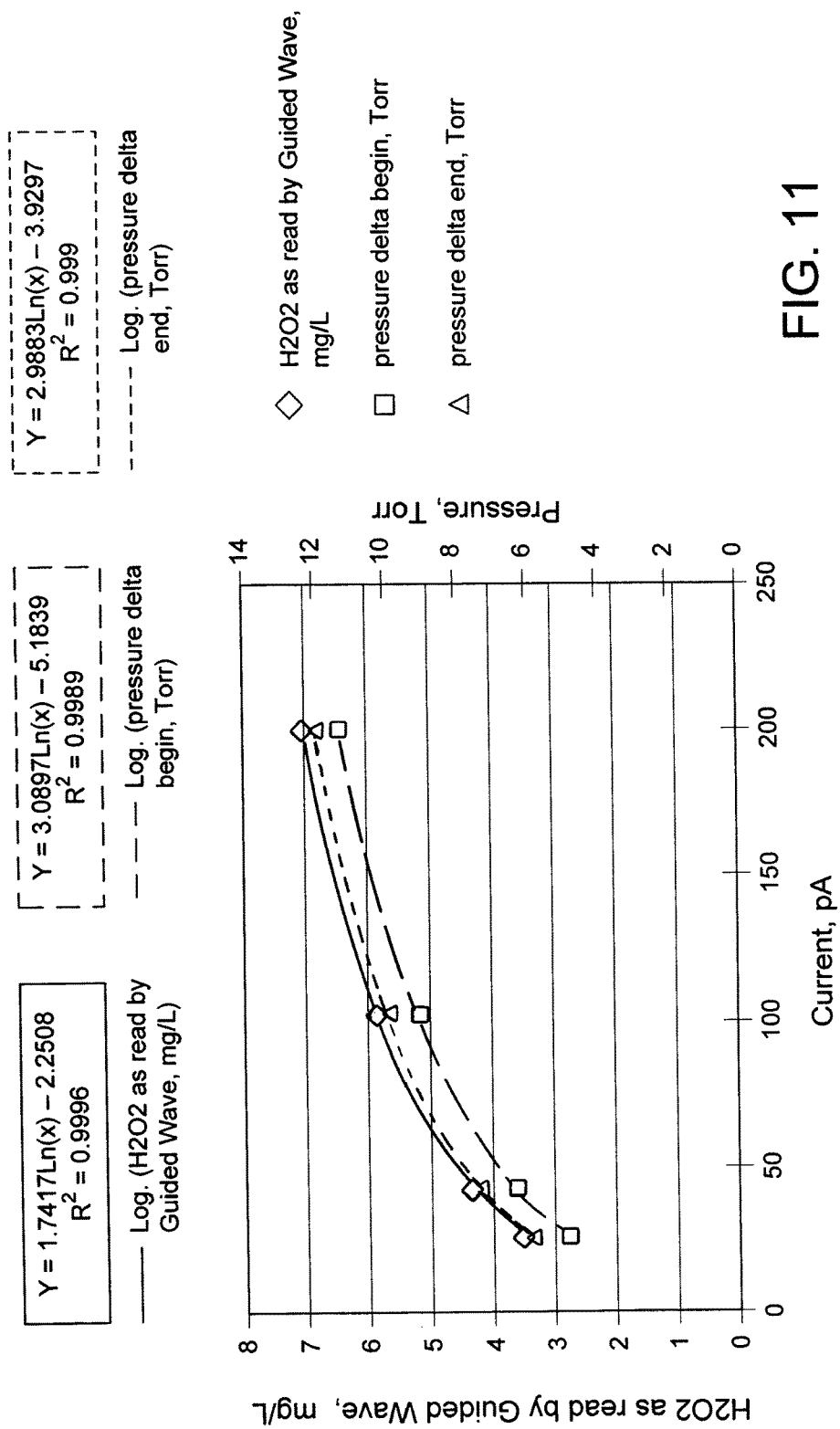
Figure 12:
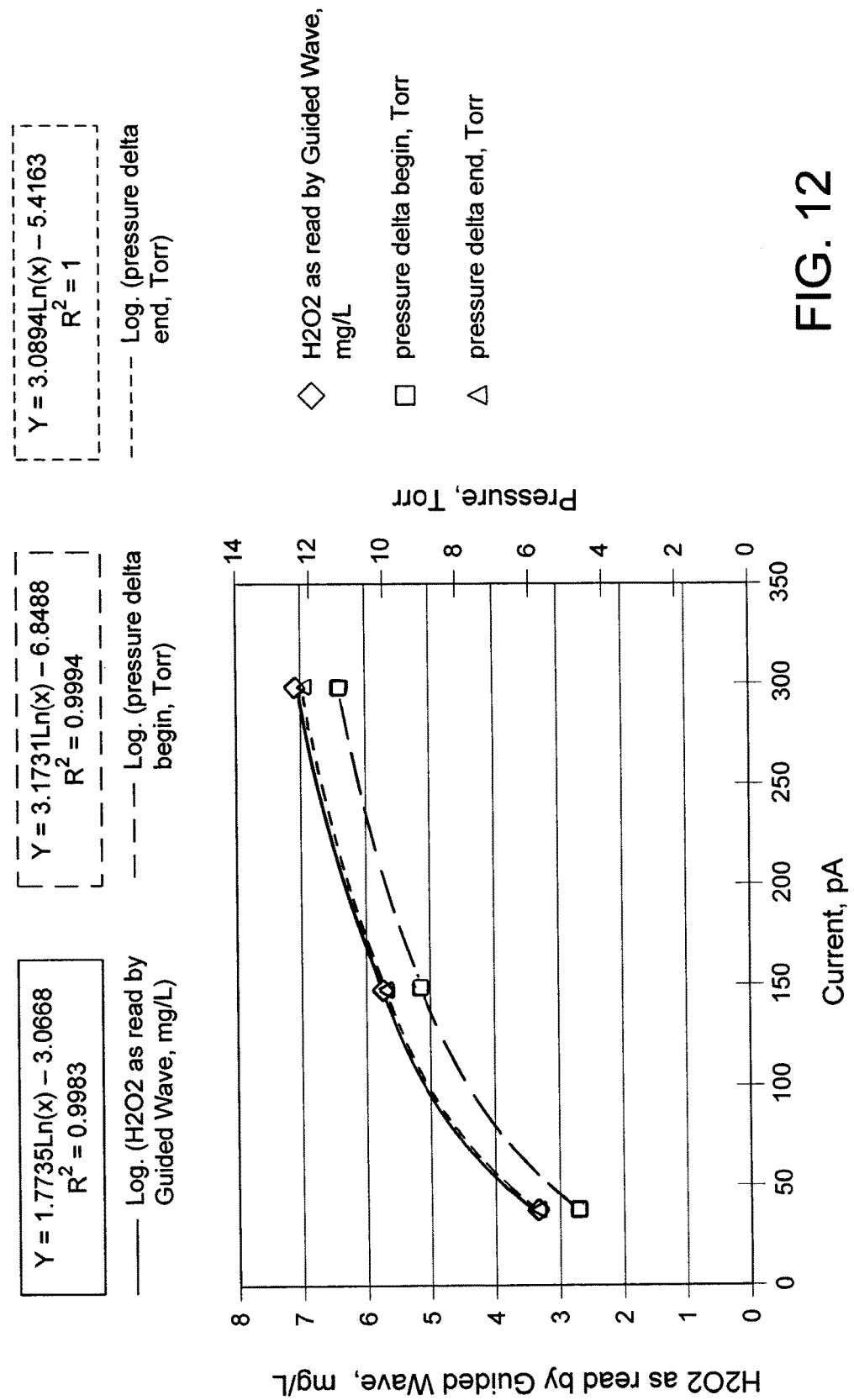

The response of the amperometric sensor and the Guided Wave IR spectrophotometer readings are shown in FIGS. 6 through 9. FIGS. 10 through 12 show that a similar exponential response with $R^2$ values exceeding 0.996 are obtained for the sensors that undergo at least 3 consecutive cycles of varying injection amounts. Equations for the Guided Wave IR spectrophotometer reading y as a function of the change in current x are as follows:

$$y=1.6607 \ln(x)-2.6361 \quad R^2=0.9958 \quad \text{(Equation 1)}$$

$$y=1.7417 \ln(x)-2.2508 \quad R^2=0.9996 \quad \text{(Equation 2)}$$

$$y=1.7735 \ln(x)-3.0668 \quad R^2=0.9983 \quad \text{(Equation 3)}$$

Using the fourth pulse of the cycles, the equations for the VHP concentration (as read by the Guided Wave IR spectrophotometer) as a function of Δ current, as well as the pressure Δ as a function of the Δ current, are calculated with Excel and Matlab for the period under vacuum. Excel is a software program available from Microsoft. Matlab is a software program available from MathWorks of Natick, Mass. The results are shown in FIGS. 10-12. The graphs in FIGS. 10-12 correspond to the raw data of FIGS. 6-8, respectively. Two different equations for pressure, denoted "begin" and "end" show a slight difference when the more conservative approach is taken of reading the Δ in pressure at the beginning of the vacuum period, in comparison to reading it at the end of the vacuum period where it is within 1 Torr higher.

Figure 13:
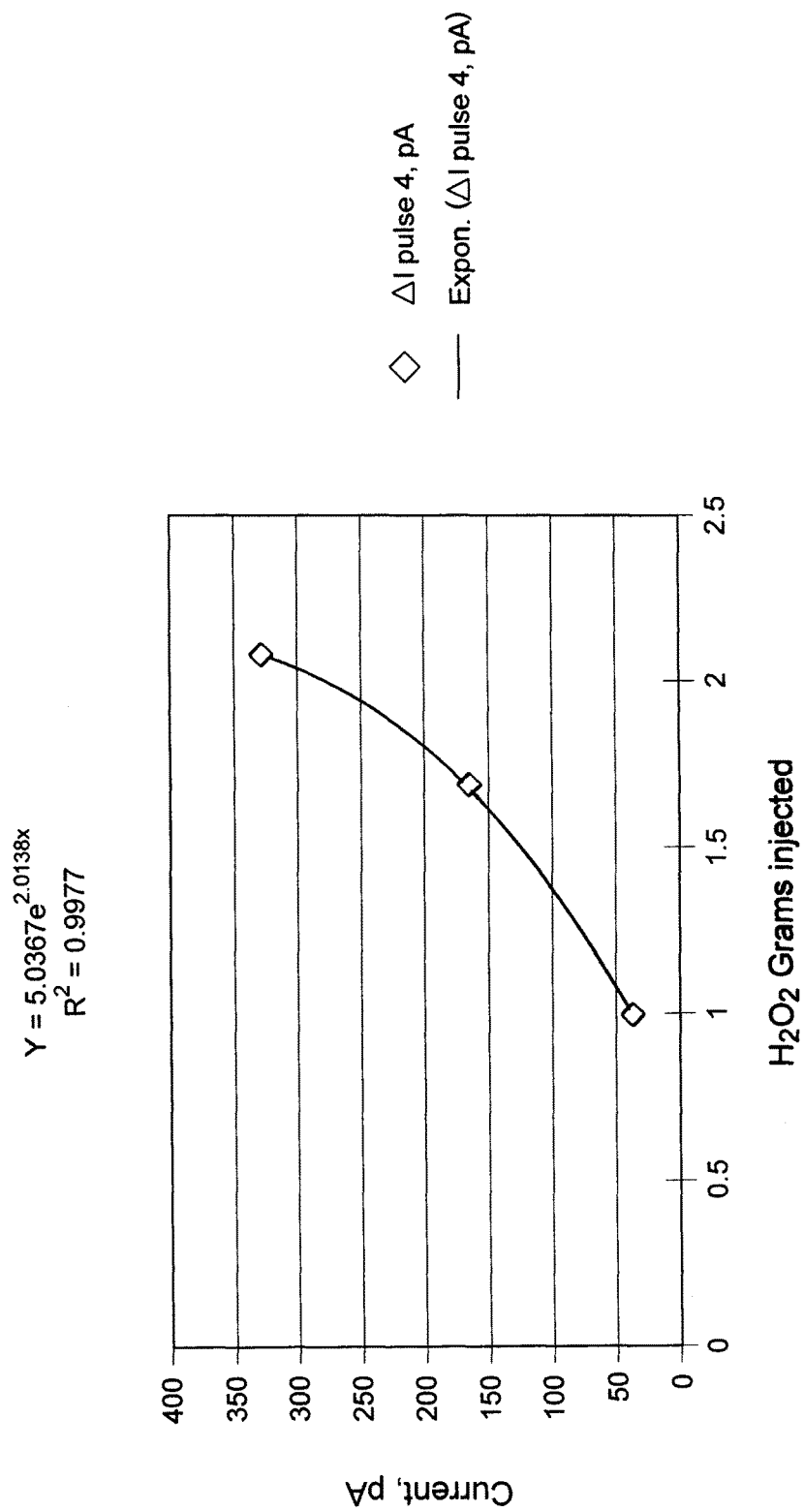
FIGS. 13-15 are charts disclosing equations determined in the Example for the Δ in current in pulse 4 as a function of the grams of hydrogen peroxide injected into the sterilizer. The values plotted in FIGS. 13-15 are taken from the raw data disclosed in FIGS. 6-8, respectively. The exponential function is fitted using Excel.
Figure 14:
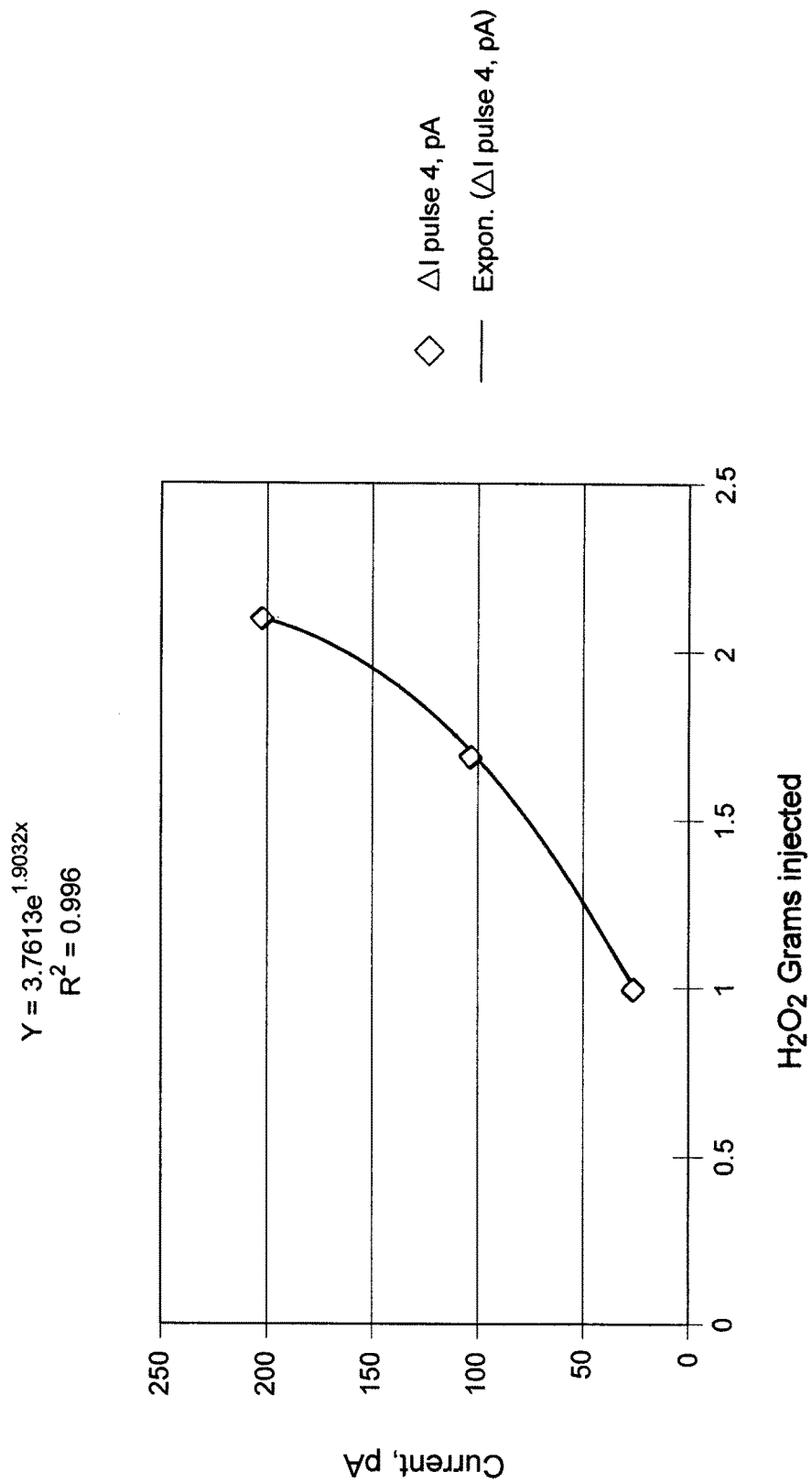
Figure 15:
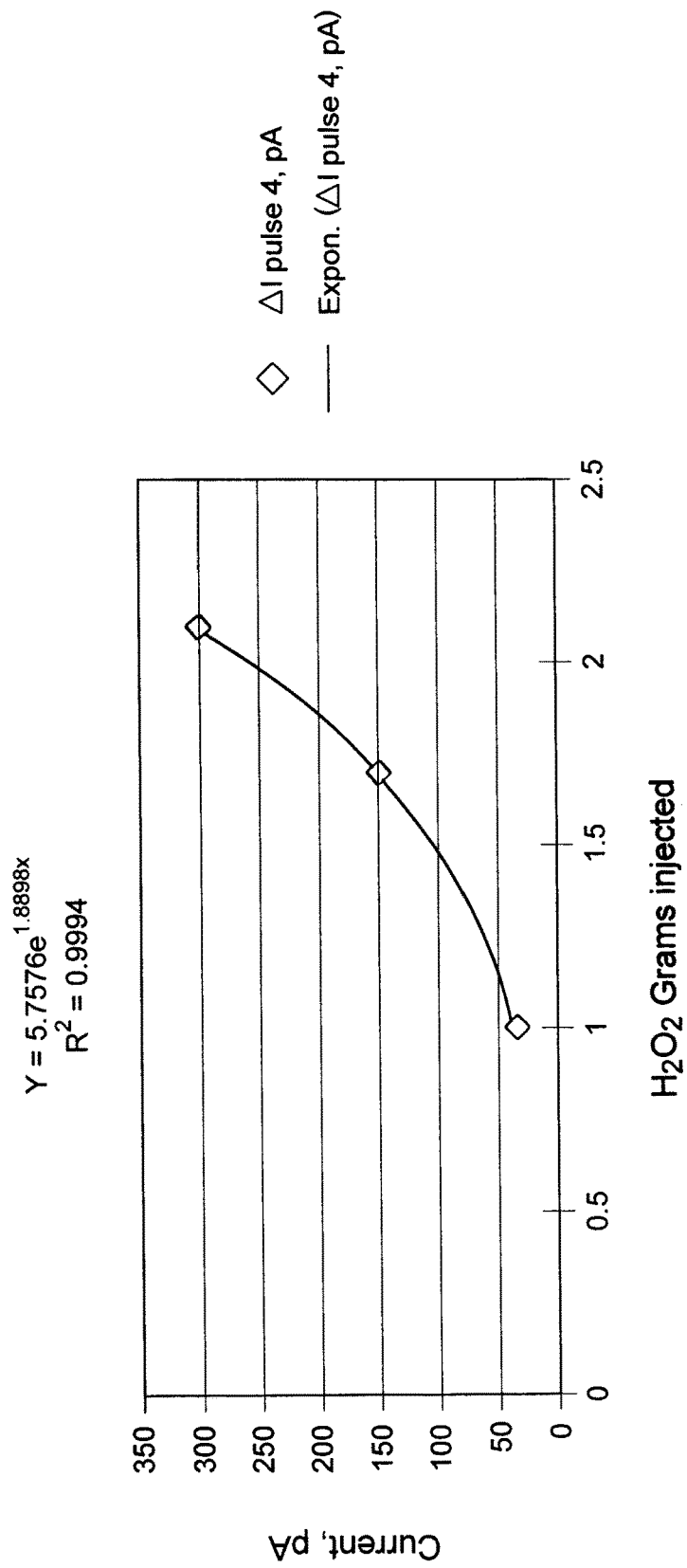

The Δ in current in pulse 4 as a function of the grams of hydrogen peroxide injected into the sterilizer is shown in FIGS. 13-15. The values plotted in FIGS. 13-15 are taken from the raw data of the three consecutive cycles in FIGS. 6-8, respectively. The exponential function is fitted with Excel.

Figure 16:
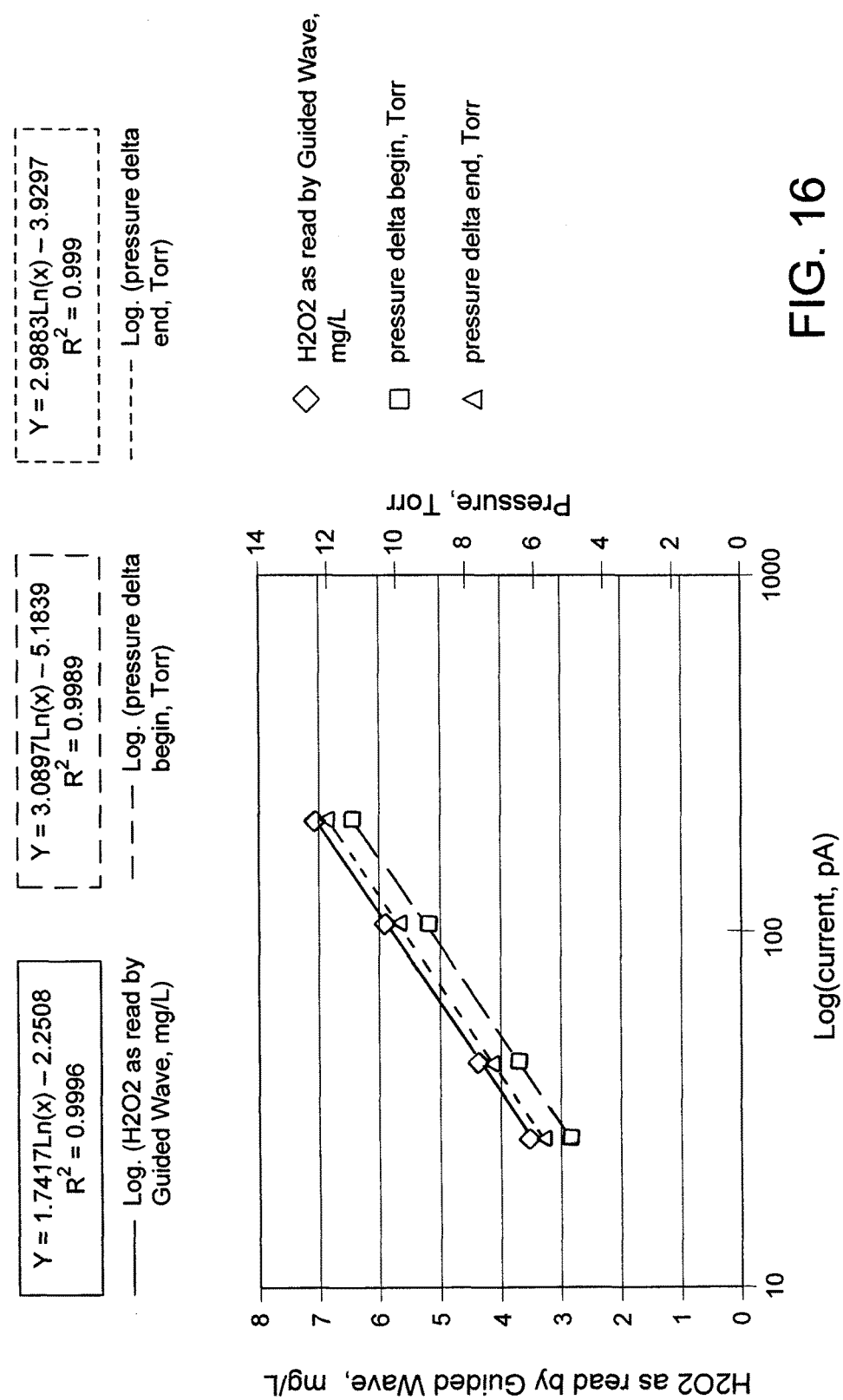
FIG. 16 is a linear-log graph representation which shows a straight line response for the results from FIGS. 10-15.

FIG. 16 is a linear-log graph representation which shows an example of the straight line response obtained for FIGS. 10 through 15. Actual current readings in real-time are measured every 3 seconds. The sampling time used in the Guided Wave's IR spectrophotometer calculation of the concentration is the last 10 seconds of data. The peak values of the Guided Wave IR spectrophotometer readings for a pulse are used in all mathematical equation calculations. The Δ in current for the pulse is used for all the mathematical equation calculations rather than a direct current reading to eliminate background current effects.

The following Table 1 summarizes the results and shows a statistical summary of how well Equation 2 (y=1.7417 Ln(x)−2.2508), predicts the actual peak Guided Wave IR spectrophotometer reading for the total change in current, I in pA. Values shown in Table 1 are for the final (4th) pulse of the cycles run.

TABLE 1

| Test Number | ΔI, pA | Actual Guided Wave Concentration, mg/L | Grams of $H_2O_2$ Injected | Predicted Concentration, mg/L, Eq. 2 | % Error = (Actual Guided Wave Concentration) − (Predicted Concentration)/ (Actual Guided Wave Concentration)) × 100 | % Difference = \|((Actual Guided Wave − Predicted Concentration)/ ((Actual Guided Wave Concentration + Predicted Concentration)/ 2)) × 100\| |
|---|---|---|---|---|---|---|
| 1 | 332.5 | 7.1 | 2.1 | 7.9 | 10.7 | 10.2 |
| 2 | 164.3 | 5.7 | 1.7 | 6.6 | 16.4 | 15.2 |
| 3 | 36.9 | 3.4 | 1.0 | 4.0 | 18.6 | 17.0 |
| 4 | 202.0 | 7.0 | 2.1 | 7.0 | 0.1 | 0.1 |
| 5 | 103.0 | 5.8 | 1.7 | 5.8 | 0.4 | 0.4 |
| 6 | 26.0 | 3.4 | 1.0 | 3.4 | 0.7 | 0.7 |
| 7 | 42.0 | 4.3 | 1.3 | 4.3 | 1.0 | 1.0 |
| 8 | 211.8 | 7.1 | 2.1 | 7.1 | 0.3 | 0.3 |
| 9 | 107.9 | 5.9 | 1.7 | 5.9 | 0.0 | 0.0 |
| 10 | 299.0 | 7.1 | 2.1 | 7.7 | 8.1 | 7.8 |
| 11 | 147.3 | 5.7 | 1.7 | 6.4 | 13.1 | 12.3 |
| 12 | 37.7 | 3.4 | 1.0 | 4.1 | 19.7 | 18.0 |

Table 1 shows the peak Guided Wave IR spectrophotometer concentration (mg/L) value predicted by Equation 2 for the total change in current for the fourth pulse in each of the samples of the experiment. The actual Guided Wave IR spectrophotometer readings for the pulses are analyzed with Minitab statistical software (available from Minitab Inc. of State College, Pa.). As shown through the remaining Minitab summaries and plots, all but 2 currents are within one standard deviation of the mean current at each injection amount (grams), and all predicted values are within a 20% error margin of the value actually obtained by the Guided Wave IR spectrophotometer for the pulse.

Descriptive Statistics: I, pA

| Grams Injected | N | N* | Mean | SE Mean | St Dsv | Minimum | Q1 | Median | Q3 | Max |
|---|---|---|---|---|---|---|---|---|---|---|
| 1.0 | 3 | 0 | 33.53 | 3.77 | 6.54 | 26.00 | 26.00 | 36.90 | 37.70 | 37.70 |
| 1.3 | 1 | 0 | 42.00 | * | * | 42.00 | * | 42.00 | * | 42.00 |
| 1.7 | 4 | 0 | 130.6 | 15.0 | 30.0 | 103.0 | 104.2 | 127.6 | 160.1 | 164.3 |
| 2.1 | 4 | 0 | 261.3 | 32.2 | 64.4 | 202.0 | 204.4 | 255.4 | 324.1 | 332.5 |

Descriptive Statistics: Actual Guided Wave IR Spectrophotometer

| Grams Injected | N | N* | Mean | SE Mean | St Dev | Coef Var | Min | Q1 | Med | Q3 | Max |
|---|---|---|---|---|---|---|---|---|---|---|---|
| 1.0 | 3 | 0 | 3.400 | 0.000 | 0.000 | 0.00 | 3.40 | 3.40 | 3.40 | 3.400 | 3.40 |
| 1.3 | 1 | 0 | 4.300 | — | — | — | 4.30 | — | 4.30 | — | 4.30 |
| 1.7 | 4 | 0 | 5.775 | 0.047 | 0.095 | 1.66 | 5.70 | 5.70 | 5.75 | 5.875 | 5.90 |
| 2.1 | 4 | 0 | 7.075 | 0.025 | 0.050 | 0.71 | 7.00 | 7.025 | 7.10 | 7.100 | 7.10 |

Descriptive Statistics: Predicted Concentration

| Grams Injected | N | N* | Mean | SE Mean | St Dev | Coef Var | Min | Q1 | Med | Q3 | Max |
|---|---|---|---|---|---|---|---|---|---|---|---|
| 1.0 | 3 | 0 | 3.833 | 0.219 | 0.379 | 9.88 | 3.40 | 3.40 | 4.00 | 4.10 | 4.10 |
| 1.3 | 1 | 0 | 4.30 | * | * | * | 4.30 | * | 4.30 | * | 4.30 |
| 1.7 | 4 | 0 | 6.175 | 0.193 | 0.386 | 6.25 | 5.80 | 5.825 | 6.15 | 6.55 | 6.60 |
| 2.1 | 4 | 0 | 7.425 | 0.221 | 0.443 | 5.96 | 7.00 | 7.025 | 7.40 | 7.85 | 7.90 |

The results indicate that none of the predicted concentrations (mg/L) using Equation 2 overlaps with the results from the inventive amperometric gas sensor. This means that injection amounts of 1 g, 1.3 g, 1.7 g, and 2.1 g of hydrogen peroxide would be uniquely discernible with the inventive amperometric gas sensor.

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A method for determining a concentration of an analyte in an enclosed space using an amperometric gas sensor, the method comprising:
placing the amperometric gas sensor in the enclosed space, the amperometric gas sensor consisting essentially of:
a solid support configured as an insulator prior to being contacted by the analyte and configured for diffusion of the analyte therethrough, the solid support consisting essentially of one or more ionically and electrically non-conductive polymers and optionally one or more non-conductive fillers, the solid support further configured to increase in electrical conductivity when in contact with the analyte;
a working electrode in contact with the solid support; and a reference electrode positioned on and in contact with the solid support, the reference electrode spaced apart and ionically and electrically insulated from the working electrode prior to the solid support being contacted by the analyte;
flowing the analyte in the enclosed space in contact with the sensor, whereby the analyte increases the electrical conductivity of the solid support; and determining the concentration of the analyte in the enclosed space using the amperometric gas sensor.

2. The method of claim 1 wherein the analyte comprises an oxidizing gas or a reducing gas.

3. The method of claim 1 wherein the analyte comprises vaporous hydrogen peroxide, ethylene oxide, ozone, or a mixture of two or more thereof.

4. The method of claim 1 wherein the analyte comprises vaporous hydrogen peroxide.

5. The method of claim 1 wherein the analyte comprises hydrogen sulfide, hydrogen sulfite, ammonia, carbon monoxide, oxalic acid, formic acid, ascorbic acid, phosphorous acid, or a mixture of two or more thereof.

6. The method of claim 1 wherein the pressure in the enclosed space is atmospheric pressure.

7. The method of claim 1 wherein the absolute pressure in the enclosed space is in the range from about 1 to about 2 atmospheres.

8. The method of claim 1 wherein the pressure in the enclosed space is below atmospheric pressure.

9. The method of claim 1 wherein the one or more ionically and electrically non-conductive polymers comprises poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly(acrylnitrile-butadiene-styrene), polyvinyl chloride, chlorinated polyether, poly(chlorotrifluoro ethylene), or a mixture of two or more thereof.

10. The method of claim 9 wherein the analyte comprises an oxidizing gas or a reducing gas.

11. The method of claim 9 wherein the analyte comprises vaporous hydrogen peroxide, ethylene oxide, ozone, or a mixture of two or more thereof.

12. The method of claim 9 wherein the wherein the analyte comprises vaporous hydrogen peroxide.

13. The method of claim 9 wherein the analyte comprises hydrogen sulfide, hydrogen sulfite, ammonia, methane, ethane, propane, butane, carbon monoxide, oxalic acid, formic acid, ascorbic acid, phosphorous acid, or a mixture of two or more thereof.

14. The method of claim 1 wherein the one or more ionically and electrically non-conductive polymers comprises poly (ethylene terephthalate).

15. The method of claim 14 wherein the analyte comprises an oxidizing gas or a reducing gas.

16. The method of claim 14 wherein the analyte comprises vaporous hydrogen peroxide, ethylene oxide, ozone, or a mixture of two or more thereof.

17. The method of claim 14 wherein the wherein the analyte comprises vaporous hydrogen peroxide.

18. The method of claim 14 wherein the analyte comprises hydrogen sulfide, hydrogen sulfite, ammonia, methane, ethane, propane, butane, carbon monoxide, oxalic acid, formic acid, ascorbic acid, phosphorous acid, or a mixture of two or more thereof.

19. A method for determining a concentration of an analyte in an enclosed space using an amperometric gas sensor, the method comprising:

placing the amperometric gas sensor in the enclosed space, the amperometric gas sensor consisting essentially of:
a solid support configured as an insulator prior to being contacted by the analyte and configured for diffusion of the analyte therethrough, the solid support consisting essentially of one or more non-conductive polymers and optionally one or more non-condutive fillers, the solid support further configured to increase in electrical conductivity when in contact with the analyte, the one or more non-conductive polymers comprising poly (ethylene terephthalate), poly (ethylene oxide), polyvinylidenefluoride, polyethylene, polypropylene, polyethylene-napthlate, polyphenylenesulfide, polycarbonate, polytetrafluoroethylene, polypropylene oxide, acrylic resin, polystyrene, poly(styrene-acrylonitrile), poly(acrylnitrile-butadiene-styrene), polyvinyl chloride, chlorinated polyether, poly(chlorotrifluoro ethylene), or a mixture of two or more thereof; a working electrode in contact with the solid support; and a reference electrode positioned on and in contact with the solid support, the reference electrode spaced apart and insulated from the working electrode prior to the solid support being contacted by the analyte;
flowing the analyte in the enclosed space in contact with the sensor, whereby the analyte increases the electrical conductivity of the solid support; and determining the concentration of the analyte in the enclosed space using the amperometric gas sensor.

20. The method of claim 19 wherein the one or more non-conductive polymers comprises poly (ethylene terephthalate).

* * * * *